(12) United States Patent
Wunberg et al.

(10) Patent No.: US 7,115,636 B2
(45) Date of Patent: Oct. 3, 2006

(54) HETROCYCLIC ARYL SULPHONAMIDES

(75) Inventors: Tobias Wunberg, Solingen (DE); Wolfgang Bender, Wuppertal (DE); Peter Eckenberg, Wuppertal (DE); Sabine Hallenberger, Wuppertal (DE); Kerstin Henninger, Wuppertal (DE); Jörg Keldenich, Wuppertal (DE); Armin Kern, Wuppertal (DE); Siegfried Raddatz, Köln (DE); Jürgen Reefschläger, Oldenburg (DE); Gunter Schmidt, Wuppertal (DE); Holger Zimmermann, Wuppertal (DE); Franz Zumpe, Wuppertal (DE); Martin Radtke, Erkrath (DE)

(73) Assignee: Bayer Healthcare AG, Leverkusen (DE)

( * ) Notice: Subject to any disclaimer, the term of this patent is extended or adjusted under 35 U.S.C. 154(b) by 141 days.

(21) Appl. No.: 10/486,054

(22) PCT Filed: Jul. 24, 2002

(86) PCT No.: PCT/EP02/08243

§ 371 (c)(1),
(2), (4) Date: Aug. 16, 2004

(87) PCT Pub. No.: WO03/014094

PCT Pub. Date: Feb. 20, 2003

(65) Prior Publication Data

US 2005/0085549 A1    Apr. 21, 2005

(30) Foreign Application Priority Data

Aug. 6, 2001    (DE) ................. 101 38 578

(51) Int. Cl.
| | | |
|---|---|---|
| A61K 31/4245 | (2006.01) | |
| A61K 31/4439 | (2006.01) | |
| A61K 31/454 | (2006.01) | |
| C07D 413/04 | (2006.01) | |
| C07D 271/06 | (2006.01) | |

(52) U.S. Cl. ............... 514/326; 514/340; 514/364; 546/209; 546/269.4; 548/131

(58) Field of Classification Search .............. 514/326, 514/340, 364; 548/131; 546/209, 269.4
See application file for complete search history.

(56) References Cited

FOREIGN PATENT DOCUMENTS

| WO | 9937291 | 7/1999 |
|----|---------|--------|
| WO | 0102350 | 1/2001 |

*Primary Examiner*—Kamal A. Saeed
*Assistant Examiner*—Jason M. Nolan

(57) ABSTRACT

The invention relates to novel sulfonamides of general formula (I)

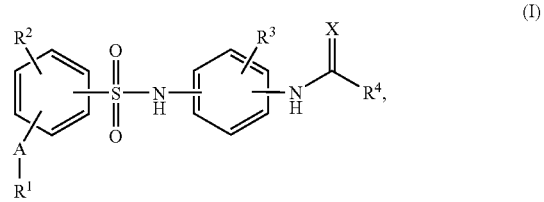

where the substituents $R^1$, $R^2$, $R^3$, $R^4$, A and X have the given meanings, pharmaceutical compositions containing them, and a method of using them as antiviral agents, in particular against cytomegaloviruses.

13 Claims, No Drawings

HETROCYCLIC ARYL SULPHONAMIDES

The present invention relates to new compounds, processes for their preparation and their use as medicaments, in particular as antiviral agents, in particular against cytomegaloviruses.

The compound 2,2-dimethyl-N-[4-[[[4-(4-phenyl-2H-1,2,3-triazol-2-yl)phenyl]-sulphonyl]amino]phenyl]-propanamide is known as having antiviral activity from WO 99/37291.

It is an object of the present invention to make available alternative agents or agents having better activity against cytomegaloviruses.

The present invention relates to compounds of the general formula (I)

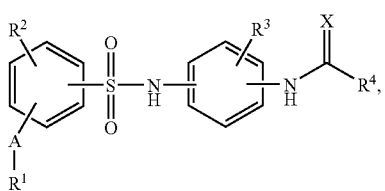

in which
R² and R³ are identical or different and represent hydrogen, hydroxyl, halogen, nitro, cyano, trifluoromethyl, trifluoromethoxy, $(C_1-C_6)$-alkyl, $(C_1-C_6)$-alkoxy or a group of the formula

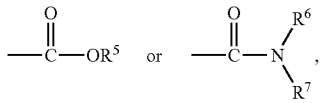

in which
R⁵, R⁶ and R⁷ are identical or different and in each case represent hydrogen or $(C_1-C_6)$-alkyl, which for its part can be substituted by one or two substituents, selected from the group consisting of hydroxyl, halogen, cyano, trifluoromethyl and trifluoromethoxy,
A represents five- or six-membered heteroaryl linked via a C atom to the adjacent phenyl ring,
R¹ represents the radical

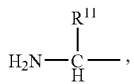

in which
R¹¹ represents the side group of an amino acid, and the amino group in R¹ can optionally be mono- or polysubstituted by $(C_1-C_6)$alkyl, alkylcarbonyl, phenyl, or
R¹ represents a straight-chain or branched $(C_1-C_5)$-alkyl radical, which for its part can be substituted by one or more groups selected from phenyl, piperidinyl, pyridinyl, thiazolyl, thienyl,

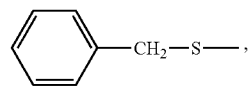

a group

in which
R¹² and R¹³ are identical or different and can represent hydrogen, $(C_1-C_6)$alkyl, alkylcarbonyl, an amino protective group, phenyl,
or
R¹ represents a radical

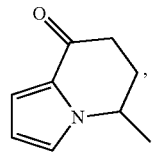

or
R¹ represents a straight-chain or branched $(C_1-C_5)$-alkyl radical, which for its part is substituted by a group

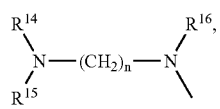

in which
R¹⁴, R¹⁵, R¹⁶ are identical or different and represent hydrogen or $(C_1-C_6)$alkyl
and
n can assume the values 2 or 3,
or
R¹ represents piperidinyl or the radical

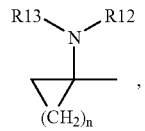

in which R¹² and R¹³ have the meaning indicated above,
n represents a number from 1 to 4 and the ring can be up to trisubstituted in an identical or different manner by halogen, $(C_1-C_6)$-alkyl, halogeno-$(C_1-C_6)$-alkyl, amino, hydroxyl,
R⁴ represents tert-butyl, which is optionally up to trisubstituted, in an identical or different manner, by hydroxyl, fluorine or chlorine, or
represents cyclopropyl or cyclobutyl, which are mono- to trisubstituted in an identical or independent manner by halogen or $(C_1-C_6)$-alkyl, $(C_1-C_6)$-alkyl being optionally substituted by hydroxyl, fluorine or chlorine, and in which
X represents oxygen or sulphur, and in which nitrogen-containing heterocycles can also be present as N-oxides, and their tautomers, stereoisomers, stereoisomeric mixtures and their pharmacologically tolerable salts.

$(C_1-C_6)$-Alkyl in the context of the invention represents a straight-chain or branched alkyl radical having 1 to 6 carbon atoms. Examples which may be mentioned are: methyl, ethyl, n-propyl, isopropyl, n-butyl, t-butyl, n-pentyl and n-hexyl.

$(C_1-C_6)$-Cycloalkyl in the context of the invention represents a cycloalkyl group having 3 to 6 carbon atoms. Examples which may be mentioned are: cyclopropyl, cyclobutyl, cyclopentyl and cyclohexyl.

$(C_3-C_6)$-Alkoxy in the context of the invention represents a straight-chain or branched alkoxy radical having 1 to 6 carbon atoms. Examples which may be mentioned are: methoxy, ethoxy, n-propoxy, isopropoxy, t-butoxy, n-pentoxy and n-hexoxy. Methoxy and ethoxy are preferred.

$(C_6-C_{10})$-Aryl in the context of the invention represents an aromatic radical having 6 to 10 carbon atoms. Preferred aryl radicals are phenyl and naphthyl.

Aralkyl in the context of the invention represents $(C_6-C_{10})$-aryl, which for its part is bonded to $(C_1-C_4)$alkyl. Benzyl is preferred.

Mono-$(C_1-C_6)$-alkylamino in the context of the invention represents an amino group having a straight-chain, branched or cyclic alkyl substituent which contains 1 to 6 carbon atoms. Examples which may be mentioned are: methylamino, ethylamino, n-propylamino, isopropylamino, cyclopropylamino, t-butylamino, n-pentylamino, cyclopentylamino and n-hexylamino.

Di-$(C_1-C_6)$-alkylamino in the context of the invention represents an amino group having two identical or different straight-chain, branched or cyclic alkyl substituents, which in each case contain 1 to 6 carbon atoms. Examples which may be mentioned are: N,N-dimethylamino, N,N-diethylamino, N-ethyl-N-methylamino, N-methyl-N-n-propylamino, N-methyl-N-cyclopropylamino, N-isopropyl-N-n-propylamino, N-t-butyl-N-methylamino, N-ethyl-N-n-pentylamino and N-n-hexyl-N-methylamino.

Heteroaryl in the context of the invention represents a monocyclic heteroaromatic having up to 3 heteroatoms from the group consisting of S, N and/or O, which is linked via a ring carbon atom of the heteroaromatic, optionally also via a ring nitrogen atom of the heteroaromatic. Examples which may be mentioned are: furan-2-yl, furan-3-yl, pyrrol-1-yl, pyrrol-2-yl, pyrrol-3-yl, thienyl, thiazolyl, oxazolyl, imidazolyl, triazolyl, pyridyl, pyrimidyl, pyridazinyl. Oxadiazolyl, thiadiazolyl are preferred.

Halogen in the context of the invention in general represents fluorine, chlorine, bromine and iodine. Fluorine, chlorine and bromine are preferred. Fluorine and chlorine are particularly preferred.

A 3- or 5-linked 1,2,4-oxadiazole represents an oxadiazole which is bonded to the phenylsulphonamide via the 3- or 5- ring carbon atom.

The side group of an amino acid is understood in the context of the invention as meaning, for example, hydrogen (glycine), methyl (alanine), propan-2-yl (valine), 2-methyl-propan-1-yl (leucine), 1-methyl-propan-1-yl (isoleucine), a propane-1,3-diyl group which is bonded to the nitrogen atom of the amino group (proline), a 2-hydroxy-propan-1,3-diyl-group which is bonded to the nitrogen atom of the amino group (hydroxyproline), a group of the formula

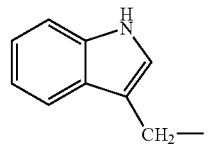

(tryptophan), a benzyl group (phenylalanine), a methylthioethyl group (methionine), hydroxymethyl (serine), p-hydroxybenzyl (tyrosine), 1-hydroxyl-ethan-1-yl (threonine), mercaptomethyl (cysteine), carbamoylmethyl (asparagine), carbamoylethyl (glutamine), carboxymethyl (aspartic acid), carboxyethyl (glutamic acid), 4-aminobutan-1-yl (lysine), 3-guanidinopropan-1-yl (arginine), imidazol-4-ylmethyl (histidine), 3-ureidopropan-1-yl (citrulline), mercaptoethyl (homocysteine), hydroxyethyl (homoserine), 4-amino-3-hydroxybutan-1-yl (hydroxylysine), 3-amino-propan-1-yl (ornithine).

Amino protective group in the context of the present invention represents a protective group which makes the amino group insensitive to some reaction conditions, but which can be removed again simply under other reaction conditions, see T. W. Greene, P. G. Wuts, *Protective Groups in Organic Synthesis*, $3^{rd}$ ed., John Wiley, New York, 1999. Preferred amino protective groups are carbamates, e.g. tert-butyloxycarbonyl (Boc), 9-fluorenylmethyloxycarbonyl (FMOC) or benzyloxy-carbonyl (Cbz-/Z-) or other oxycarbonyl derivatives.

Preferred salts in the context of the invention are physiologically acceptable salts of the compounds according to the invention.

Physiologically acceptable salts of the compounds according to the invention can be acid addition salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, citric acid, fumaric acid, maleic acid or benzoic acid.

Salts which can be mentioned are, however, also salts with customary bases, such as, for example, alkali metal salts (e.g. sodium or potassium salts), alkaline earth metal salts (e.g. calcium or magnesium salts) or ammonium salts, derived from ammonia or organic amines such as, for example, diethylamine, triethylamine, ethyldiisopropylamine, procaine, dibenzylamine, N-methylmorpholine, dihydroabietylamine, 1-ephenamine or methylpiperidine, or derived from natural amino acids such as, for example, glycine, lysine, arginine or histidine.

The compounds according to the invention can exist in stereoisomeric forms, which either behave as image and mirror image (enantiomers), or which do not behave as image and mirror image (diastereomers). The invention relates both to the enantiomers or diastereomers and to their respective mixtures. The racemic forms, just like the diastereomers, can be separated into the stereoisomerically uniform constituents in a known manner.

Moreover, the invention also comprises prodrugs of the compounds according to the invention. "Prodrugs" are designated according to the invention as those derivatives of the compounds of the general formula (I) which can be biologically less active or even inactive themselves, but after administration are converted into the corresponding biologically active form under physiological conditions (for example metabolically, solvolytically or in another manner).

The abovementioned radical definitions, which are general or indicated in preferred ranges apply to the final products of the formula (I) and also correspondingly to the starting substances or intermediates needed in each case for preparation.

The radical definitions specifically indicated in the respective combinations or preferred combinations of radicals are arbitrarily also replaced by radical definitions of other combinations independently of the combinations of the radicals respectively indicated.

The invention preferably relates to compounds of the general formula (I), in which
$R^2$ and $R^3$ are identical or different and represent hydrogen or halogen,
A represents the radical (A-I)

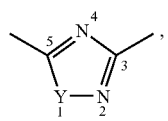
(A-I)

which is linked via one of the carbon atoms of positions 3 or 5 to the adjacent phenyl ring,
and in which
Y represents oxygen, or
A represents the radical (A-II)

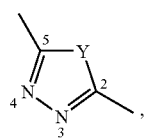
(A-II)

which is linked via one of the carbon atoms of positions 2 or 5 to the adjacent phenyl ring,
and in which
Y represents oxygen,
$R^1$ represents the radical

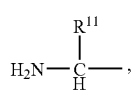

in which
$R^{11}$ represents the side group of an amino acid, and the amino group in $R^1$ can optionally be mono- or polysubstituted by $(C_1-C_6)$-alkyl, alkylcarbonyl, an amino protective group, phenyl, or
$R^1$ represents a straight-chain or branched $(C_1-C_5)$-alkyl radical, which for its part can be substituted by one or more groups selected from phenyl, piperidinyl, pyridinyl, thiazolyl, thienyl,

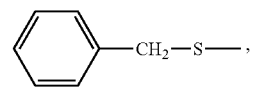

a group

in which
$R^{12}$ and $R^{13}$ are identical or different and can represent hydrogen, $(C_1-C_6)$-alkyl, alkylcarbonyl, an amino protective group, phenyl,
or
$R^1$ represents a straight-chain or branched $(C_1-C_5)$-alkyl radical, which for its part is substituted by a group

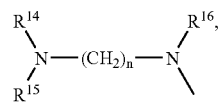

in which
$R^{14}$, $R^{15}$, $R^{16}$ are identical or different and represent hydrogen or methyl
and
n can assume the values 2 or 3, or
$R^1$ represents piperidin-3-yl or the radical

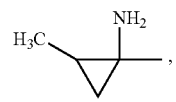

$R^4$ represents tert-butyl, which is optionally up to trisubstituted, in an identical or different manner, by hydroxyl, fluorine or chlorine, or
represents cyclopropyl or cyclobutyl, which is substituted in the α-position to the carbonyl group or thiocarbonyl group by methyl, which for its part is optionally substituted by hydroxyl, fluorine or chlorine, and in which
X represents oxygen, and in which nitrogen-containing heterocycles can also be present as N-oxides, and their tautomers, stereoisomers, stereoisomeric mixtures and their pharmacologically tolerable salts.

The invention relates particularly preferably to compounds of the general formula (I), in which
R² and R³ represent hydrogen,
A represents one of the radicals

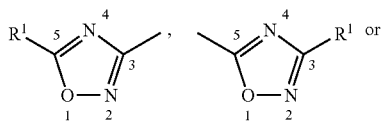

R¹ represents the radical

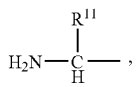

in which
R¹¹ represents the side group of an amino acid, and the amino group in R¹ can optionally be mono- or polysubstituted by methyl, alkylcarbonyl, an amino protective group, phenyl, or R¹ represents a straight-chain or branched $(C_1-C_5)$-alkyl radical, which for its part can be substituted by one or more groups selected from phenyl, piperidinyl, pyridinyl, thiazolyl, thienyl,

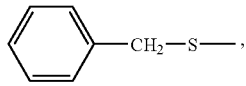

a group

in which
R¹² and R¹³ are identical or different and can represent hydrogen, methyl, alkylcarbonyl, an amino protective group, phenyl, or R¹ represents a straight-chain or branched $(C_1-C_5)$ alkyl radical, which for its part is substituted by a group

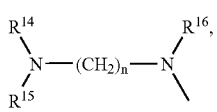

in which
R¹⁴, R¹⁵, R¹⁶ are identical or different and represent hydrogen or methyl
and
n can assume the values 2 or 3, or
R¹ represents piperidin-3-yl or the radical

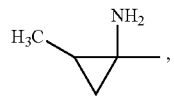

R⁴ represents tert-butyl, which is optionally up to trisubstituted, in an identical or different manner, by hydroxyl, fluorine or chlorine, or
represents cyclopropyl or cyclobutyl, which is substituted in the α- position to the carbonyl group or thiocarbonyl group by methyl, which for its part is optionally substituted by hydroxyl, fluorine or chlorine, and in which
X represents oxygen, and in which nitrogen-containing heterocycles can also be present as N-oxides, and their tautomers, stereoisomers, stereoisomeric mixtures and their pharmacologically tolerable salts.

In a preferred embodiment, the invention relates to compounds of the general formula (Ia)

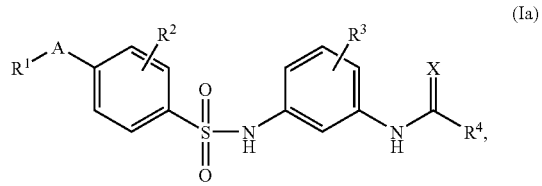

in which
R¹, R², R³, R⁴, A and X have the meanings indicated above.

In a further preferred embodiment, the invention relates to those compounds of the general formula (I), in which
R⁴ represents one of the radicals

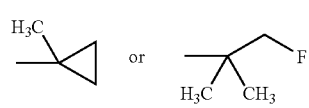

In a further preferred embodiment, the invention relates to those compounds of the general formula (I), in which
A represents a 3-linked 1,2,4-oxadiazole.

Very particularly preferred compounds of the present invention are sulphonamides which are selected from the group consisting of the following compounds:

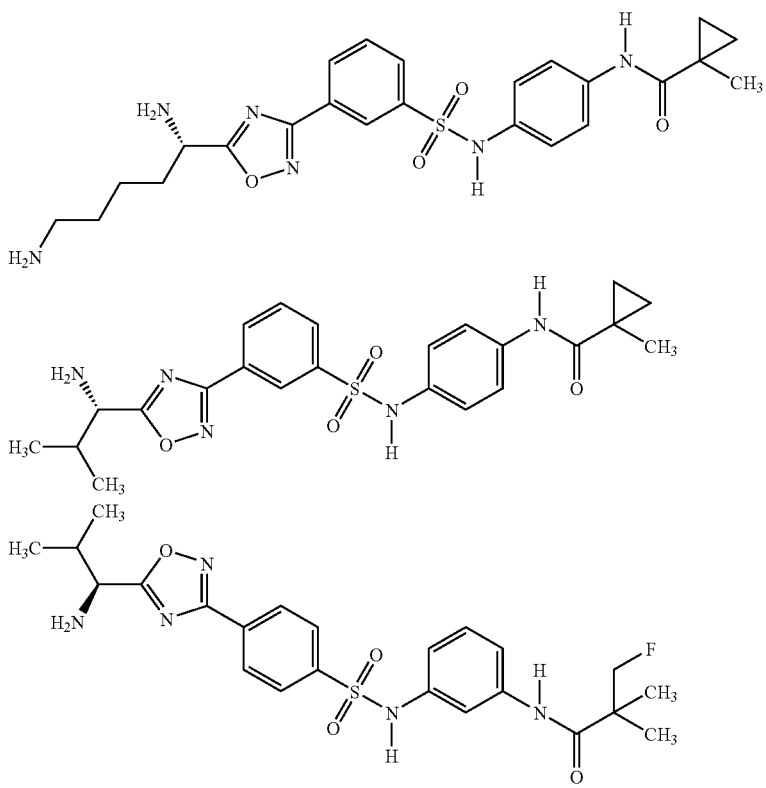

The invention further relates to processes for the preparation of compounds of the general formula (I), characterized in that

[A] nitro-anilines of the general formula [A-1]

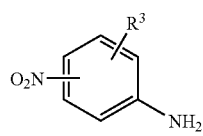

[A-1]

in which $R^3$ has the meaning indicated above, are reacted with compounds of the general formula [A-2]

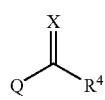

[A-2]

in which

X and $R^4$ have one of the meanings indicated above, and

Q represents a leaving group, e.g. halogen, preferably chlorine or bromine, in inert solvents in the presence of a base to give compounds of the general formula [A-3]

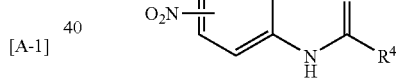

[A-3]

in which

X, $R^3$ and $R^4$ have one of the meanings indicated above, and

[B] the nitro-aromatics of the general formula [A-3] are reduced, for example in the presence of transition metal catalysts and hydrogen, in inert solvents to give aromatic amines of the general formula [B-1]

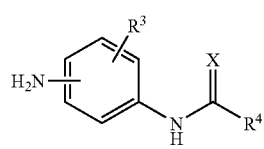

[B-1]

in which

X, $R^3$ and $R^4$ have one of the meanings indicated above, and

[C] amines of the general formula [B-1] are reacted with sulphonic acid derivatives of the general formula [C-1]

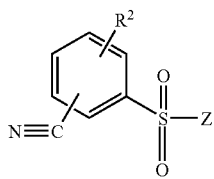

[C-1]

in which

R² has the meaning indicated above, and

Z represents a leaving group, e.g. halogen, preferably chlorine or bromine, in inert solvents, in the presence of a base, to give compounds of the general formula [C-2]

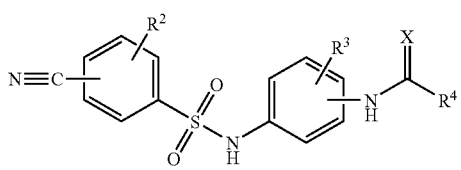

[C-2]

in which

X, R², R³ and R⁴ have one of the meanings indicated above, and

[D] the nitriles of the general formula [C-2] are reacted in polar protic solvents, for example alcohols, at elevated temperature, preferably the boiling temperature of the solvent, in presence of a base with hydroxylamine to give amidoximes of the general formula [D-1]

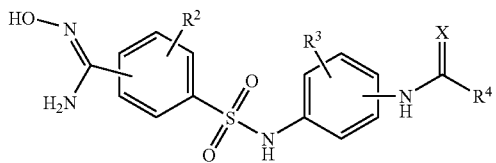

[D-1]

in which

X, R², R³ and R⁴ have one of the meanings indicated above, and

[E] amidoximes of the general formula [D-1] are acylated with a carboxylic acid of the general formula [E-1]

R¹—COOH  [E-1]

in which

R¹ has the meaning indicated above and amino groups contained in R¹ are present in protected form with protective groups known from peptide chemistry, such as, for example, the Boc protective group, in the presence of a condensing agent, for example benzotriazolyl-N-oxy-tris(dimethylamino)phosphonium hexafluorophosphate (PyBOP), or other activating reagents and acid chlorides known from peptide chemistry, and a base in a polar, aprotic solvent, for example tetrahydrofuran, the acylated amidoxime is isolated as a crude product and subsequently cyclized to the 1,2,4-oxadiazole in a high-boiling, polar solvent, for example DMF, at elevated temperature.

The process according to the invention for the preparation of 1,2,4-oxadiazoles linked via position 3 is illustrated by way of example by the following reaction scheme:

Scheme 1:

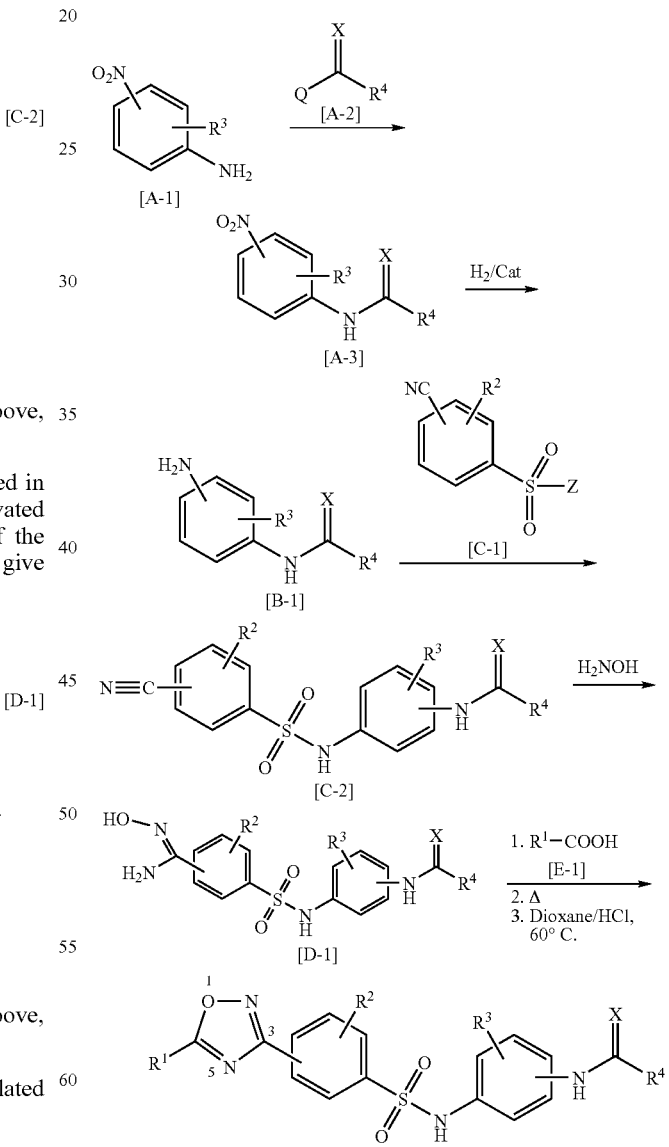

The invention further relates to processes for the preparation of compounds of the general formula (I), characterized in that

[F] sulphonyl halides of the general formula [F-1]

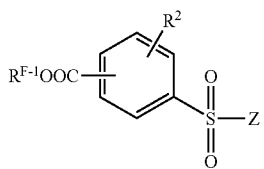
[F-1]

in which

R² and Z have the meaning indicated above, and $R^{F-1}$ represents $(C_1–C_4)$-alkyl, aralkyl or a carboxylic acid protective group, are reacted in the presence of a base with anilines of the general formula [B-1] to give sulphonamides of the general formula [F-2]

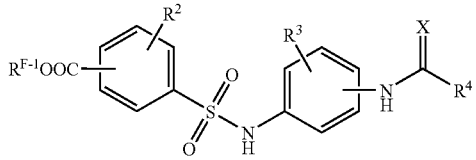
[F-2]

in which $R^{F-1}$, R², R³, R⁴ and X have the meaning indicated above, and subsequently the group $R^{F-1}$ is removed from the compounds of the general formula [F-2], for example in the presence of hydroxyl anions, and reacted to give sulphonamides of the general formula [F-3],

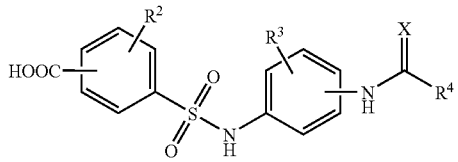
[F-3]

and

[G] amid-oximes of the general formula [G-1]

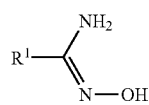
[G-1]

in which

R¹ has the meaning indicated above, are condensed with compounds of the general formula [F-3] to give compounds of the general formula [G-2],

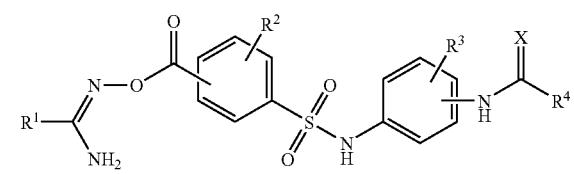
[G-2]

in which

R¹, R², R³, R⁴ and X have the meaning indicated above, and

[H] compounds of the general formula [G-2] are cyclized thermally to the 5-linked 1,2,4-oxadiazoles of the general formula [H-1] according to the invention

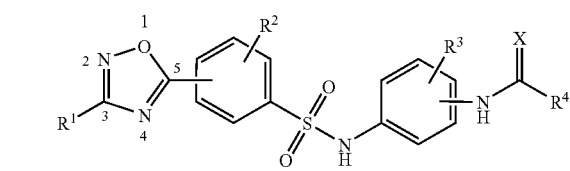
[H-1]

in which

R¹, R², R³, R⁴ and X have the meaning indicated above.

The process according to the invention is illustrated by way of example by the following reaction schemes:

Scheme 2:

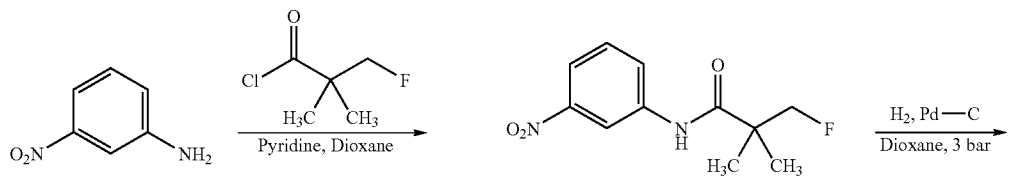

-continued
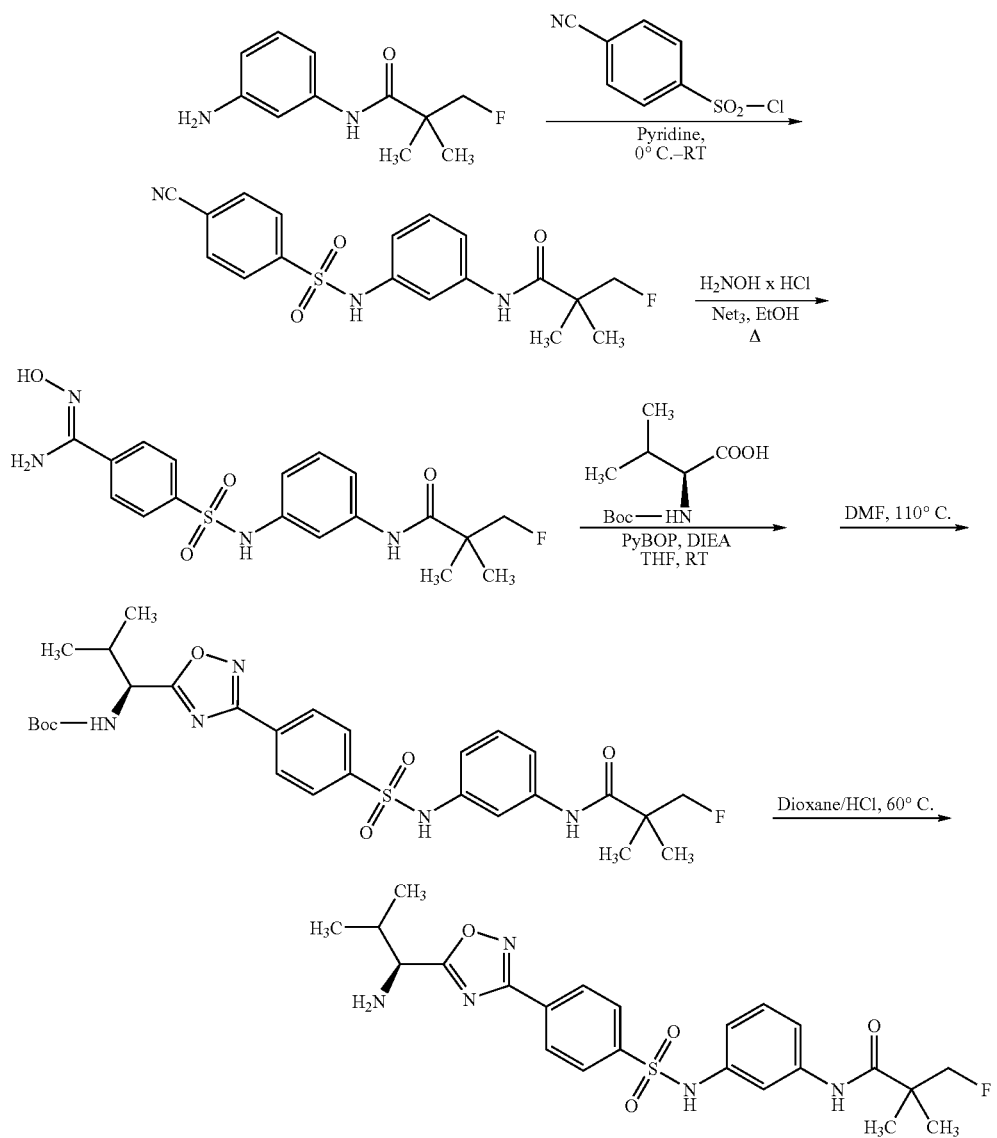
Scheme 3:
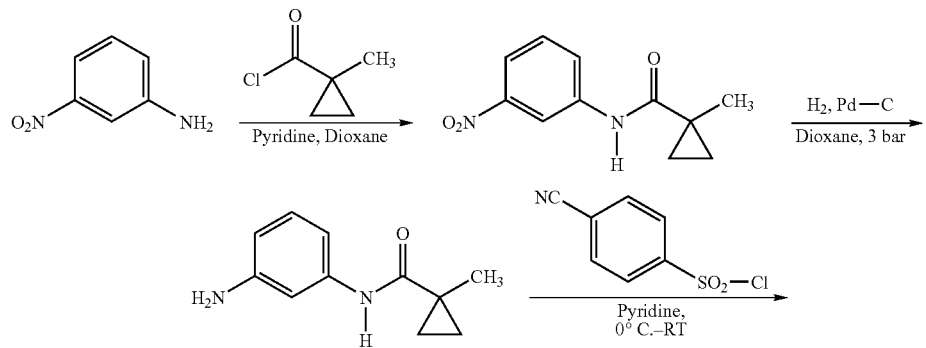

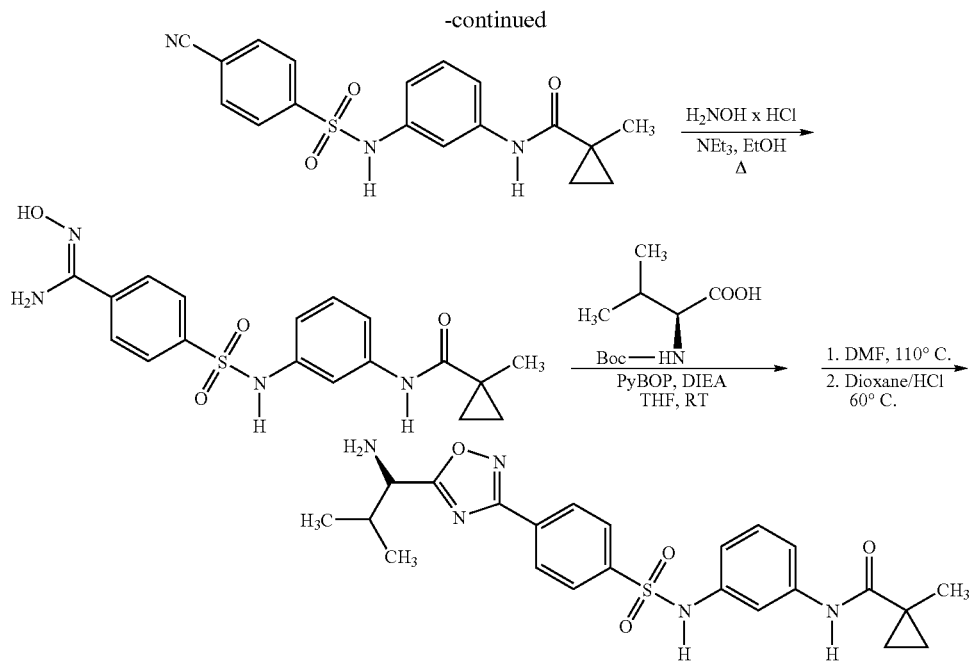

Suitable solvents for all process steps are the customary inert solvents, which do not change under the reaction conditions. These preferably include organic solvents such as ethers, e.g. diethyl ether, glycol mono- or dimethyl ether, dioxane or tetrahydrofuran, or alcohols such as methanol, ethanol, n-propanol, iso-propanol, n-butanol or tert-butanol, or hydrocarbons such as benzene, toluene, xylene, cyclohexane or petroleum fractions or halogenohydrocarbons such as methylene chloride, chloroform, carbon tetrachloride, or dimethyl sulphoxide, dimethylform-amide, hexamethylphosphoramide, ethyl acetate, pyridine, triethylamine or picoline. It is likewise possible to use mixtures of the solvents mentioned, optionally also with water. Methylene chloride, tetrahydrofuran, dioxane and dioxane/water and in particular the solvents mentioned in the section of the text "General working procedures" are particularly preferred.

Suitable bases are organic amines such as tri-($C_1$–$C_6$)-alkylamines, for example triethylamine, or heterocycles such as pyridine, methylpiperidine, piperidine or N-methylmorpholine. Triethylamine and pyridine are preferred.

The bases are in general employed in an amount from 0.1 mol to 5 mol, preferably from 1 mol to 3 mol, in each case based on 1 mol of the compounds of the general formulae [A-1], [B-1], [C-2], [D-1] and [E-1].

Suitable carboxylic acid protective groups are those which make the carboxylic acid group insensitive to certain reaction conditions, but which can be simply removed again under other reaction conditions, see T. W. Greene, P. G. Wuts, *Protective Groups in Organic Synthesis*, $3^{rd}$ ed., John Wiley, New York, 1999. Preferred carboxylic acid protective groups are esters such as alkyl esters or aralkyl esters, in particular benzyl esters and benzyl derivatives.

The reactions can be carried out at normal pressure, but also at elevated or reduced pressure (e.g. 0.5 to 3 bar). In general, they are carried out at normal pressure.

The reactions are carried out in a temperature range from 0° C. to 150° C., preferably at 0° C. to 30° C. and at normal pressure. The reaction of the compounds [G-2] to [H-1] is carried out at elevated temperature, preferably at temperatures above 100° C.

The reductions can in general be carried out by means of hydrogen in inert organic solvents such as dimethylformamide, alcohols, ethers or esters of acetic acid, or their mixtures, using catalysts such as Raney nickel, palladium, palladium on carbon or platinum, or using hydrides or boranes, or using inorganic reducing agents such as, for example, tin(II) chloride, in inert solvents, optionally in the presence of a catalyst. Palladium on carbon is preferred.

The reaction can be carried out at normal or at elevated pressure (e.g. 1 to 5 bar). In general, it is carried out at normal pressure. Hydrogenations are preferably carried out under elevated pressure, in general at 3 bar.

The reductions are in general carried out in a temperature range from 0° C. to +60° C., preferably at +10° C. to +40° C.

Suitable solvents for the acylation are customary organic solvents, which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogeno-hydrocarbons such as dichloromethane, trichloromethane, tetrachloromethane, dichloroethylene, trichloroethylene or chlorobenzene, or ethyl acetate, or triethylamine, pyridine, dimethylformamide, acetonitrile or acetone. It is likewise possible to use mixtures of the solvents mentioned. Dichlormethane, tetrahydrofuran and pyridine are preferred.

The acylation is carried out in the abovementioned solvents at temperatures from 0° C. to +150° C., preferably at room temperature to +100° C. and at normal pressure.

The compounds of the general formulae [A-1], [A-2], [C-1], [E-1], [F-1] and [G-1] are known per se or can be prepared by methods known from the literature.

Further compounds of the general formula (I), in which A represents a 1,3,4-oxadiazole, can be prepared, for example, according to Scheme 4 as given below on a polymeric support, e.g. formyl resin (from Nova), 0.78 mmol/g, called "formyl resin" below, using the IRORI system according to the "Split & Mix" method:

Scheme 4:
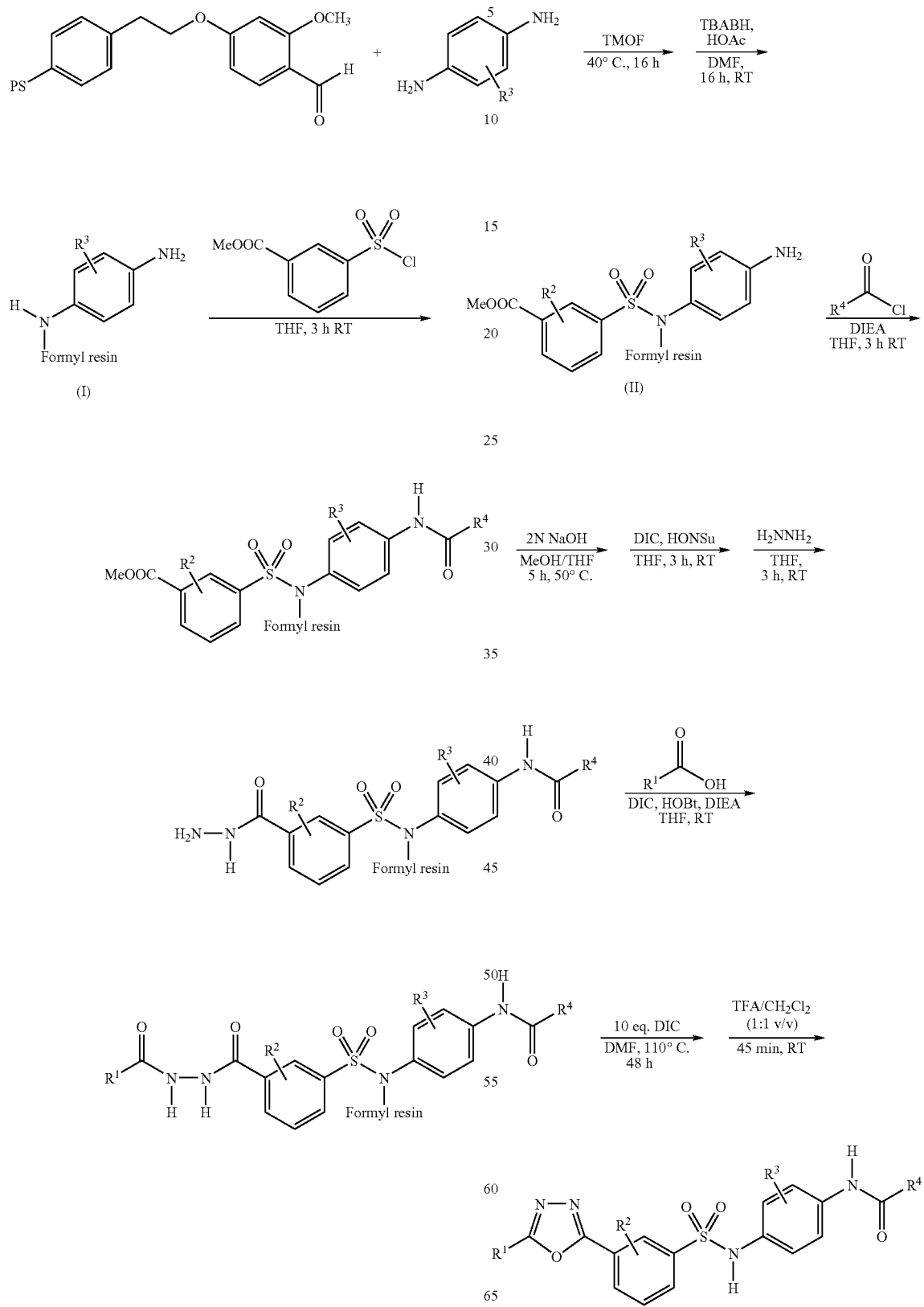

The processes shown according to Scheme 4 thus allow the preparation of further compounds of the general formula (I) according to the invention, in which
X represents oxygen
and
A represents the radical (A-II)

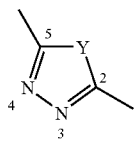
(A-II)

which is linked to the adjacent phenyl ring via one of the carbon atoms of positions 2 or 5,
and in which
Y represents oxygen,
by cyclizing hydrazides of the general formula [H-2]

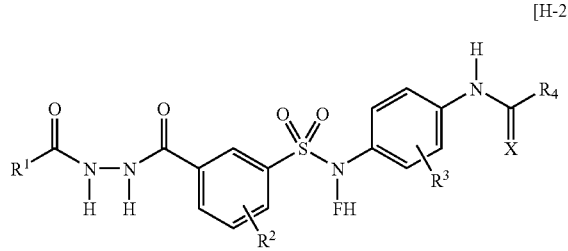
[H-2]

in which X, $R^1$, $R^2$, $R^3$, $R^4$ have one of the meanings indicated above,
and
FH represents hydrogen, an amino protective group or a polymeric support,
with removal of water to give the compounds of the general formula (I).

The compounds of the general formula (I) according to the invention have an unforeseeable surprising spectrum of action. They have an antiviral action against representatives of the group consisting of Herpes viridae, particularly against human cytomegalovirus (HCMV). They are thus suitable for the treatment and prophylaxis of diseases which are caused by Herpes viridae, in particular of diseases which are caused by human cytomegaloviruses.

The compounds of the general formula (I) can be used on account of their particular properties for the production of medicaments which are suitable for the prophylaxis or treatment of illnesses, in particular viral diseases.

On account of their properties, the compounds according to the invention are valuable active compounds for the treatment and prophylaxis of human cytomegalovirus infections and diseases caused thereby. Indication areas which can be mentioned are, for example:
1) Treatment and prophylaxis of HCMV infections in AIDS patients (retinitis, pneumonitis, gastrointestinal infections).
2) Treatment and prophylaxis of cytomegalovirus infections in bone marrow and organ transplantation patients who are suffering, often in a life-threatening manner, from HCMV pneumonitis, HCMV encephalitis, and also from gastrointestinal and systemic HCMV infections.
3) Treatment and prophylaxis of HCMV infections in newborn children and infants.
4) Treatment of an acute HCMV infection in pregnant women.
5) Treatment of HCMV infection in immunosuppressed patients in cancer and cancer therapy.

The new active compounds can be employed on their own and, if required, also in combination with other antiviral active compounds such as, for example, gancyclovir or acyclovir.

Biological Test Descriptions:

In vitro Action:

Anti-HCMV (anti-human cytomegalovirus) and anti-MCMV (anti-murine cytomegalovirus) cytopathogenicity tests:

The test compounds were employed as 50 millimolar (mM) solutions in dimethyl sulfoxide (DMSO). Ganciclovir, foscarnet and cidofovir served as reference compounds. After the addition of 2 µl in each case of the 50, 5, 0.5 and 0.05 mM DMSO stock solutions to 98 µl each of cell culture medium in row 2 A-H in duplicate, 1:2 dilutions using 50 µl each of medium up to row 11 of the 96-well plate were carried out. The wells in rows 1 and 12 each contained 50 µl of medium. 150 µl each of a suspension of $1\times10^4$ cells (human lung fibroblasts [HELF]) were then pipetted into the wells (row 1=cell control) or a mixture of HCMV-infected and non-infected HELF cells (M.O.I.=0.001–0.002), i.e. 1–2 infected cells to 1000 non-infected cells, was pipetted into rows 2–12. Row 12 (without substance) served as a virus control. The final test concentrations were 250–0.0005 µM. The plates were incubated at 37° C./5% $CO_2$ for 6 days, i.e. until all cells were infected in the virus controls (100% cytopathogenic effect [CPE]). The wells were then fixed by addition of a mixture of formalin and Giemsa's stain and stained (30 minutes), washed with double-distilled water and dried at 50° C. in a drying oven. The plates were then evaluated visually using an overhead microscope (Plaque multiplier from Technomara).

It was possible to determine the following data from the test plates:

$EC_{50}$ (HCMV)=substance concentration in µM which inhibited the CPE (cytopathic effect) by 50% in comparison to the untreated virus control;

SI (selectivity index)=$CC_{50}$ (HELF)/$EC_{50}$ (HCMV).

The anti-MCMV test was carried out in a modification of the process described above for HCMV with the following changes: A cell-free virus suspension was mixed with a concentrated cell suspension (3T3 mouse cells) and incubated for 15 minutes for the adsorption of the viruses, before it was diluted to $1.3\times10^5$ cells/ml with medium with an end multiplicity of infection (M.O.I.) of 0.05–0.1 and distributed into the wells using 150 µl each. The incubation time was 5 days.

Representative activity data for the compounds according to the invention are presented in Table 1:

TABLE 1

| Example No. | HELF CC$_{50}$ [µM] | HCMV EC$_{50}$ [µM] | SI HCMV | 3T3 CC$_{50}$ [µM] | MCMV EC$_{50}$ [µM] | SI MCMV |
|---|---|---|---|---|---|---|
| 1 | >250 | 0.028 | >8929 | 18 | 0.035 | 514 |
| 2 | 118 | 0.35 | 337 | 2.5 | 0.05 | 50 |
| 3 | >250 | 0.074 | 3378 | 63 | 0.074 | 851 |

In vivo Action:

MCMV Mortality Test:

Animals:

2–3 week-old female immunocompetent mice (12–14 g), strain Balb/C AnN or CD1 were obtained from commercial breeders (Bomholtgaard, Iffa, Credo). The animals were not kept under sterile conditions.

Virus Growth:

Murine cytomegalovirus (MCMV), strain Smith, was repeatedly passaged in female CD1 mice in vivo. 21 days after intraperitoneal infection ($2 \times 10^4$ plaque forming units/0.2 ml/mouse), the salivary glands were removed, taken up in a three-fold volume of Minimal Essential Medium (MEM)+10% foetal calf serum (FCS) and homogenized with the aid of an Ultraturrax. 10% DMSO v/v was added, 1 ml aliquots were prepared and the virus suspension was stored at −140° C. After serial dilution of the salivary gland isolate in steps of ten, the titre determination was carried out in cell culture on NIH 3T3 cells after staining with Giemsa solution, and the determination of the lethal dose in vivo was carried out in 2–3 week-old Balb/C mice.

Virus Infection of the Experimental Animals Treatment and Evaluation:

2–3 week-old female immunocompetent Balb/C mice (12–14 g) were infected intraperitoneally with $3 \times 10^5$ PFU/0.2 ml/mouse. Starting 6 hours after the infection, the mice were treated perorally with substance twice daily (8.00 and 16.00 hours) over a period of 5 days. The dose was 3, 10, 30 or 90 mg/kg of body weight, the administration volume 10 ml/kg of body weight. The substances were formulated in the form of a 0.5%-strength Tylose suspension with 2% DMSO. In the period from 4–8 days after infection, the placebo-treated control animals die. The evaluation is carried out by the determination of the percentage of surviving animals after substance treatment in comparison with the placebo-treated control group.

HCMV Xenograft Gelfoam® Model:

Animals:

3–4 week-old female immunodeficient mice (16–18 g), Fox Chase SCID or Fox Chase SCID-NOD, were obtained from commercial breeders (Bomholtgaard, Jackson). The animals were kept in isolators under sterile conditions (including litter and feed).

Virus Growth:

Human cytomegalovirus (HCMV), strain DavisSmith, was grown in vitro on human embryonic foreskin fibroblasts (NHDF cells). After infection of the NHDF cells with a multiplicity of infection (M.O.I) of 0.01, the virus-infected cells were harvested 5–7 days later and stored at −140° C. with 10% DMSO in the presence of Minimal Essential Medium (MEM), 10% foetal calf serum (FCS). After serial dilution of the virus-infected cells in steps of ten, the titre was determined on 24-well plates of confluent NHDF cells after vital staining with Neutral Red.

Preparation of the Sponges Transplantation, Treatment and Evaluation:

Collagen sponges 1×1×1 cm in size (Gelfoam®; from Peasel & Lorey, Order No. 407534; K. T. Chong et al., Abstracts of 39$^{th}$ Interscience Conference on Antimicrobial Agents and Chemotherapy, 1999, p. 439) are firstly wetted with phosphate-buffered saline (PBS), the included air bubbles are removed by degassing and they are then stored in MEM+10% FCS. $1 \times 10^6$ virus-infected NHDF cells (infection with HCMV-Davis M.O.I=0.01) are detached 3 hours after infection and added dropwise to a moist sponge in 20 µl of MEM, 10% FCS. 12–13 hours later, the infected sponges are incubated with 25 µl of PBS/0.1% BSA/1 mM DTT containing 5 ng/µl of basic Fibroblast Growth Factor (bFGF). For transplantation, the immunodeficient mice are anaesthetized with Avertin, the dorsal fur is removed with the aid of a dry razor, the epidermis is opened 1–2 cm, relaxed and the moist sponges are transplanted under the dorsal skin. The operation wound is closed with tissue adhesive. 24 hours after transplantation, the mice were treated perorally with substance twice daily over a period of 8 days (8.00 and 16.00 hours). The dose was 10 or 30 mg/kg of body weight, the administration volume 10 ml/kg of body weight. The substances were formulated in the form of a 0.5% strength Tylose suspension with 2% DMSO. 10 days after transplantation and 16 hours after the last substance administration, the animals were killed painlessly and the sponge was removed. The virus-infected cells were released from the sponge by collagen digestion (330 U/1.5 ml) and stored at −140° C. in the presence of MEM, 10% foetal calf serum, 10% DMSO. The evaluation is carried out after serial dilution of the virus-infected cells in steps of ten by titre determination on 24-well plates of confluent NHDF cells after vital staining with Neutral Red. The number of infectious virus particles after substance treatment was determined in comparison with the placebo-treated control group.

The test described below serves for the investigation of the substances according to the invention with a view to their side effect potential with respect to induction of cytochrome P450 enzymes.

Investigation of the Induction of Cytochrome P450 Enzymes in Human Liver Cell Cultures:

Primary human hepatocytes were cultured for 8 days at a cell density of $2.5 \times 10^5$ cells between two layers of collagen in 24 well microtitre plates at 37° C. under 5% CO$_2$. The cell culture medium was changed daily.

After 48 hours in culture, the hepatocytes were treated for 5 days in duplicate with different concentrations of the test substances in comparison with the inductors rifampicin (50 µM) and phenobarbital (2 mM). The final concentrations of the test substances were 0.1–10 µg/ml.

From the cell cultures, the inductive effect of the test substances on the cytochrome (CYP) P450 enzymes 1A2, 2B6, 2C19 and 3A4 was determined on day 8 by addition of the substrates 7-ethoxyresorufin (CYP1A2), [$^{14}$C]S-mephenytoin (CYP2B6 and 2C19) and [$^{14}$C]testosterone (CYP3A4). The inductive potential of the test substances was determined from the enzyme activities thus measured of CYP1A2-, 2B6-, 2C19- and 3A4-treated cells in comparison with untreated cells.

The new active compounds can be converted in a known manner into the customary formulations, such as tablets, coated tablets, pills, granules, aerosols, syrups, emulsions, suspensions and solutions, using inert, non-toxic, pharmaceutically suitable vehicles or solvents. In this connection, the therapeutically active compound should in each case be present in a concentration of approximately 0.5 to 90% by weight of the total mixture, i.e. in amounts which are sufficient in order to achieve the dose range indicated.

The formulations are prepared, for example, by extending the active compounds using solvents and/or vehicles, optionally using emulsifying agents and/or dispersing agents, it being possible, for example, in the case of the use of water as a diluent optionally to use organic solvents as auxiliary solvents.

Administration is carried out in a customary manner, preferably orally, parenterally or topically, in particular perlingually or intravenously.

For the case of parenteral administration, solutions of the active compounds using suitable liquid carrier materials can be employed.

In general, it has proved advantageous in the case of intravenous administration to administer amounts of approximately 0.001 to 10 mg/kg, preferably approximately 0.01 bis 5 mg/kg of body weight to achieve efficacious results, and in the case of oral administration the dose is approximately 0.01 to 25 mg/kg, preferably 0.1 to 10 mg/kg of body weight.

In spite of this, it can optionally be necessary to depart from the amounts mentioned, namely depending on the body weight or on the type of administration route, on the individual behaviour towards the medicament, the manner of its formulation and the time or interval at which administration takes place. Thus in some cases it can be adequate to manage with less than the abovementioned minimum amount, while in other cases the upper limit mentioned must be exceeded. In the case of the administration of relatively large amounts, it may be advisable to divide these into a number of individual administrations over the course of the day.

Abbreviations:

| | |
|---|---|
| Aloc-Cl | allyl chloroformate |
| DCM | dichloromethane |
| DIC | N,N'-diisopropylcarbodiimide |
| DIEA | diisopropylethylamine |
| DMF | dimethylformamide |
| eq. | equivalents |
| HOAc | acetic acid |
| HOBt | hydroxybenzotriazole |
| HONSu | N-hydroxysuccinimide |
| MTP | microtitre plate |
| PS- | polystyrene resin- |
| PyBOP | benzotriazolyl-N-oxy-tris(dimethylamino)phosphonium hexafluorophosphate |
| Rt | reaction time |
| RT | room temperature |
| TBABH | tetrabutylammonium borohydride |
| TFA | trifluoroacetic acid |
| THF | tetrahydrofuran |
| TMOF | trimethyl orthoformate |

General Working Procedure for the Reaction of Compounds of the Formula [A-1] with Compounds of the Formula [A-2] (GWP 1):

1.0 eq of [A-1] is dissolved in dioxane (0.2 M solution), treated with 2.5 eq. of pyridine, the solution is cooled to 5° C. and then 1.1 eq. of [A-2], in which Q preferably represents chlorine, is added dropwise as a 1.0 M solution. The batch is stirred further at 5° C. for 30 min, then the cooling is removed and stirring is continued at room temperature for 16 h. The batch is added to $H_2O$, and the precipitated product is filtered off with suction, washed with $H_2O$ and dried in a high vacuum.

General Working Procedure for the Hydrogenation of Compounds of the Formula [A-3] (GWP 2):

0.14 mol of the compounds [A-3] is dissolved in 500 ml of DMF or ethanol and treated under argon with a suspension of 6.0 g of 10% strength Pd—C. It is then hydrogenated at a hydrogen pressure of 3 bar. As soon as the conversion is complete (TLC or HPLC checking), the Pd—C catalyst is filtered off and the solvent is removed in vacuo. The crude products of the general formula [B-1] are reacted further without further purification.

General Working Procedure for the Sulphonylation of the Compounds of the General Formula [B-1] (GWP 3):

Under argon, 1.0 eq. of the compounds [B-1] are dissolved in dioxane (0.2 M solution) and treated with 2.5 eq. of pyridine. After the mixture had been stirred at room temperature for 30 min, 1.1 eq. of the compounds of the general formula [C-1], in which Z preferably represents chlorine, dissolved in dioxane (1.0 M solution) are added and the mixture is stirred at room temperature for 16 h. The solution is then added to $H_2O$ and extracted three times with DCM. The organic phase is washed with satd. $NaHCO_3$ solution, dried over $Na_2SO_4$, filtered and the solvent is removed in vacuo. The residue [C-2] is dried in a high vacuum and then reacted further without further purification.

General Working Procedure for the Synthesis of Compounds of the General Formula [D-1] from Compounds of the General Formula [C-2] (GWP 4):

The compounds of the formula [C-2] (1.0 eq.) are dissolved in ethanol (0.1 M solution), the solution is treated with hydroxylamine hydrochloride (1.5 eq.) and triethylamine (1.6 eq.), then heated under reflux for 4 h and stirring is continued at room temperature for 16 h. The solvent is removed in vacuo, the residue is taken up in ethyl acetate and extracted 3× with water, the organic phase is dried over $MgSO_4$, filtered and freed of the solvent in vacuo. The residue [D-1] is dried in a high vacuum.

General Working Procedure for the Reaction of the Compounds of the General Formula [D-1] with Compounds [E-1] (GWP 5):

1.0 eq. of the compounds of the general formula [D-1], 1.05 eq. of carboxylic acid [E-1] and 1.1 eq. PyBOP are introduced in THF (0.1 M solution), the suspension is treated with 1.1 eq. of N,N-diisopropylethylamine and the resulting solution is stirred at room temperature for 16 h. The batch is then diluted with 10 ml of DCM and extracted once each with 1 N HCl, satd. $NaHCO_3$ solution and satd. NaCl solution. The organic phase is dried over $Na_2SO_4$, filtered and the solvent is removed in vacuo. The crude product is directly reacted further.

General Working Procedure for the Synthesis of a 1,2,4-oxadiazole from the Crude Product (GWP 6) Obtained According to GWP 5:

1.0 mmol of crude product obtained according to GWP 5 is taken up in 10 ml of DMF and the solution is heated to 110° C. As soon as the conversion is complete (TLC or HPLC checking, about 2–16 h), the batch is diluted with DCM and extracted twice with $H_2O$. The combined aqueous phases are extracted twice with DCM, the organic phases are combined and dried over $Na_2SO_4$, filtered and the solvent is removed in vacuo. The compounds of the general formula (I) thus obtained are purified by chromatography on silica gel (cyclohexane/ethyl acetate) or by preparative HPLC.

General Working Procedure for the Removal of a Boc Protective Group (GWP 7):

1.0 mmol des Boc-protected amine are taken up in 10 ml of a mixture of TFA/CH$_2$Cl$_2$ or TFA/dioxane (1:1 v/v), and the solution is stirred at RT. As soon as the conversion is complete (about 45 min), the solvent is removed in vacuo, the residue is taken up in DCM and the mixture is extracted twice with satd. NaHCO$_3$ solution. The combined aqueous phases are extracted twice with CH$_2$Cl$_2$, the organic phases are combined and dried over Na$_2$SO$_4$, filtered and the solvent is removed in vacuo. The product is purified by chromatography on silica gel (cyclohexane/ethyl acetate) or by preparative HPLC.

General Working Procedures for the Syntheses Using Polymeric Supports:

General Working Procedure for the Synthesis of the 1,3,4-oxadiazoles According to Scheme 4:

The reactions according to Scheme 4 were carried out on a polymeric support using the IRORI system according to the "Split & Mix" method familiar to the solid-phase chemist with 4 carboxylic acid chlorides, 24 carboxylic acids and both meta- and para-isomers of the phenylenediamine or sulphonyl chloride. In this connection, the first two stages were carried out in a flask, the other stages in the IRORI minikans (100 mg of resin per Kan).

Synthesis of the Starting Resins (I) and (II) for the Syntheses on the Polymeric Support According to Scheme 4:

Reductive Amination of formyl Resin (from Nova Biochem, 0.78 mmol/g):

The formyl resin (1.0 eq.) is suspended in TMOF/DMF (100 ml per 12.5 g of resin) in a flask and treated with the diamine (6.0 eq.). The suspension is shaken at 40° C. for 16 h and then treated with a freshly prepared solution of TBABH (4.0 eq.) and HOAc (16.0 eq.) in DMF. After 8 h at RT, the solvent is filtered off and the resin is treated again with the reduction solution. After a further 16 h at RT, the solvent is filtered off with suction and the resin (I) is washed 2× in each case with 200 ml each of 50% strength HOAc, DMF, THF and DCM and dried in a high vacuum.

Sulphonylation of Polymer-Bound Phenylendiamine:

The resin (I) (1.0 eq.) is taken up in THF and treated with the sulphonyl chloride (1.5 eq.). The suspension is shaken at RT for 16 h and the solvent is filtered off with suction. The resin (II) is then washed 2× each with 100 ml each of 50% strength HOAc, DMF, THF and DCM and dried in a high vacuum.

Resin Preparation for the IRORI System:

The resins of type II are divided as a suspension (per 3.0 g of resin: 30 ml DMF/DCM 2:1 v/v) into 96 minikans each (1 ml of suspension per Kan), washed with DCM three times in each case and the Kans are dried in vacuo.

Reaction Sequence (IRORI):

Acylation Using Acid Chlorides:

The Kans are sorted, taken up in THF and treated with 5.0 eq. of DIEA and 5.0 eq. of acid chloride, briefly evacuated, and shaken at RT for 3 h. The reaction solutions are then separated off, and the Kans are combined and washed (2× each 50% strength HOAc, DMF, THF, DCM).

Hydrazide Synthesis:

The combined Kans are taken up in a mixture of 2 N NaOH/MeOH/THF (5:7:15 v/v), briefly evacuated, and stirred at 50° C. for 5 h. The Kans are then washed (2× each 50% strength HOAc, DMF, THF, DCM) and dried in vacuo. The Kans are then taken up using THF, treated with 5 eq. of DIC and 10 eq. of HONSu and shaken at RT for 3 h. The mixture is filtered off, washed 2× with THF and then taken up again using THF and treated with 3 eq. of hydrazine hydrate. After a further 3 h at RT, the mixture is filtered off with suction and the Kans are washed with 2× each of 50% strength HOAc, DMF, THF, DCM.

Acylation with Carboxylic Acids/DIC/HOBt:

The carboxylic acids (3 eq.) are treated with 3 eq. of DIC, 6 eq. of DIEA and 6 eq. of HOBt in THF. After activation at RT for 60 min, the solution is added to the previously sorted Kans and shaken at RT for 16 h. The Kans are then combined, washed (2× each 50% strength HOAc, DMF, THF, DCM) and dried in vacuo.

Cyclization to the 1,3,4-oxadiazole:

The combined Kans are taken up in DMF, treated with DIC (10 eq.), briefly evacuated and stirred at 110° C. for 48 h. The Kans are then washed (2× each 50% strength HOAc, DMF, THF, DCM) and dried in vacuo.

Removal from the Polymeric Support:

After sorting into IRORI removal blocks, the Kans are cut up, the resin is divided in FlexChem blocks and the products are removed using 1.0 ml each of TFA/DCM (1:1 v/v) for 45 min at RT in a Deep-Well MTP. The resin is subsequently washed with 1 ml of DCM and the solvent is evaporated.

Starting Compounds:

EXAMPLE I

1-Methyl-N-(3-nitrophenyl)-cyclopropanamide

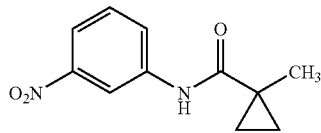

This compound is prepared from 80.0 g of 3-nitroaniline according to GWP 1.

Yield: 107 g (81% of theory)

EXAMPLE II

3-Fluoro-2,2-dimethyl-N-(3-aminophenyl)-propanamide

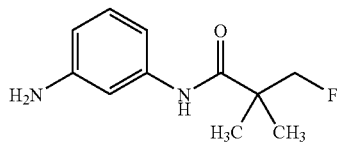

This compound is prepared from 3-nitroaniline without purification of the intermediate stage according to GWP 1 and GWP 2.

Yield: 85% of theory (over 2 stages)

EXAMPLE III

1-Methyl-N-(3-aminophenyl)-cyclopropanamide

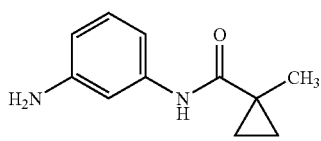

This compound is prepared from 107 g of the compound from Example I according to GWP 2.

Yield: 80 g (87% of theory)

EXAMPLE IV

3-Fluoro-2,2-dimethyl-N-(3-{[(4-methylphenyl)sulphonyl]amino}phenyl)-propanamide

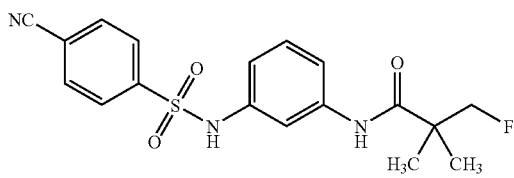

This compound is prepared from 18.68 g of the compound from Example II according to GWP 3.

Yield: 19.96 g (78% of theory)

EXAMPLE V

N-{3-[({4-[Amino(hydroxyimino)methyl]phenyl}(sulphonyl)amino]phenyl}-3-fluoro-2,2-dimethyl-propanamide

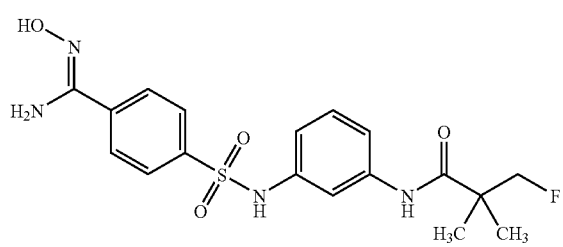

This compound is prepared from 10.0 g of the compound from Example IV according to GWP 3.

Yield: 10.5 g (97% of theory)

EXAMPLE VI

N-(3-{[(4-Phenyl)sulphonyl]amino}phenyl)-1-methylcyclopropanecarboxamide

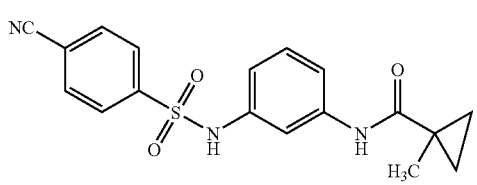

This compound is prepared from 80.0 g of the compound from Example III according to GWP 3.

Yield: 159 g of crude product (>100% of theory)

EXAMPLE VII

N-{3-[({4-[Amino(hydroxyimino)methyl]phenyl}(sulphonyl)amino]phenyl}-1-methylcyclopropanecarboxamide

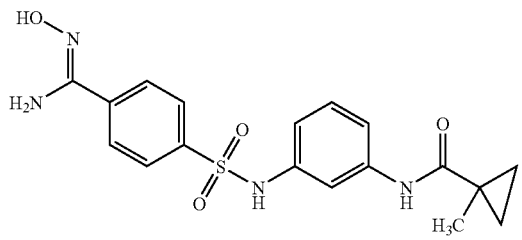

This compound is prepared from 158 g of the compound from Example VI according to GWP 3.

Yield: 148 g (83% of theory)

WORKING EXAMPLES

The working examples for 3-linked 1,2,4-oxadiazoles mentioned below were prepared from the compounds of the type Example V according to GWP 5, GWP 6 and GWP 7.

EXAMPLE 1

N-(4-{[(3-{5-[(1S)-1,5-Diaminopentyl]-1,2,4-oxadiazol-3-yl}phenyl)sulphonyl]-amino}(phenyl)-1-methylcyclopropanecarboxamide

EXAMPLE 2

N-(3-{[(4-{5-[(1S)-1-Amino-2-methylpropyl]-1,2,4-oxadiazol-3-yl}phenyl)sulphonyl]amino}phenyl)-1-methylcyclopropanecarboxamide

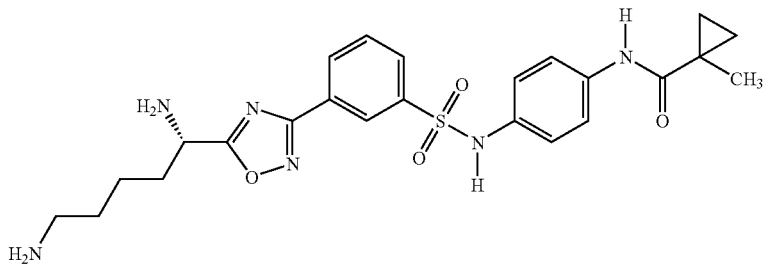

100 mg (0.257 mmol) of the amidoxime, which is prepared analogously to Examples IV and V, 93.6 mg (0.27 mmol) of Boc-Lys(Boc)-OH and 147 mg (0.27 mmol) of PyBOP are introduced into 3 ml of THF, the suspension is treated at room temperature with 36.6 mg (56.66 mmol) of N,N-Diisopropylethylamine and the resulting clear solution is stirred at room temperature for 16 h. The batch is then diluted with 15 ml of $CH_2Cl_2$ and extracted once each with 10 ml each of 1N HCl, satd. $NaHCO_3$ solution and satd. NaCl solution. The organic phase is dried over $Na_2SO_4$, filtered and the solvent is removed in vacuo. The crude product (184 mg) is taken up in 7 ml of DMF and the solution is stirred at 110° C. for 2.5 h. The batch is then diluted with 15 ml of $CH_2Cl_2$ and the organic phase is extracted twice with 10 ml each of $H_2O$. The combined aqueous phases are extracted twice with 10 ml each of $CH_2Cl_2$, the organic phases are combined and dried over $Na_2SO_4$, filtered and the solvent is removed in vacuo. The product is purified by chromatography on silica gel 60 using cyclohexane/ethyl acetate 1:1 v/v. Yield: 141 mg (79%), white solid.

For removal of the Boc protective groups, the product is dissolved in 5 ml of a TFA/DCM solution (1:1 v/v) and the reaction mixture is stirred at RT for 30 min. The solvent is then removed in vacuo, the residue is taken up in 3 ml of 1N NaOH, adjusted to pH=9 using 1N HCl and the crude product is added to a chromatography column containing a weakly acidic ion exchanger (Amberlite IRC50, 20–50 mesh), the column is washed with $MeOH/H_2O$ mixtures (1:9→3:6) and the product is then eluted using 5% $NH_3$ in $MeOH/H_2O$ (5:95 v/v). The solvent is removed in vacuo and the residue is taken up in 1 ml of $H_2O$ and lyophilized.

Yield: 15.7 mg (18%), white lyophilizate. $^1$H-NMR (200 MHz, DMSO): δ=0.47–0.60 (m, 2 H), 0.90–1.01 (m, 2 H), 1.22–1.53 (m, 4 H), 1.36 (s, 3 H), 1.65–1.90 (m, 2 H), 2.63 (t, 2 H), 4.12 (t, 1 H), 6.80 (d, 2 H), 7.21 (d, 2 H), 7.59 (t, 1 H), 7.84 (d, 1 H), 8.04 (d, 1 H), 8.33 (s, 1 H), 8.88 (s, 1 H).

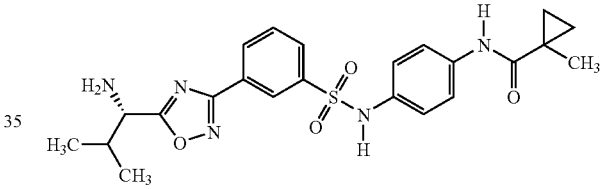

183 mg (1.42 mmol) of N,N-diisopropylethylamine, 294 mg (1.35 mmol) of Boc-Val-OH and 737 mg (1.42 mmol) of PyBOP are introduced into 15 ml of THF, stirred at room temperature for 30 min, then treated with 500 mg (1.29 mmol) of the amidoxime and the solution is stirred at room temperature for 16 h. The batch is then diluted with 30 ml of $CH_2Cl_2$ and extracted once each with 20 ml each of 1N HCl, satd. $NaHCO_3$ solution and satd. NaCl solution. The organic phase is dried over $Na_2SO_4$, filtered and the solvent is removed in vacuo. The crude product (1.18 g) is taken up in 45 ml of DMF and the solution is stirred at 110° C. for 8 h. The solvent is then removed in vacuo, the residue is dissolved in 20 ml of a TFA/DCM solution (1:1 v/v) and the reaction mixture is stirred at RT for 45 min. The solvent is then removed in vacuo, the residue is taken up in 30 ml of DCM and the organic phase is extracted twice with 30 ml each of $H_2O$. The combined aqueous phases are extracted twice with 30 ml each of $CH_2Cl_2$, and the organic phases are combined and dried over $Na_2SO_4$, filtered and the solvent is removed in vacuo. The product is purified by preparative HPLC (CromSil C18, 250×30, flow 50 ml/min, running time: 38 min, detection at 210 nm, gradient 10% ACN (3 min)→90% ACN (31 min)→90% ACN (34 min)→10% ACN (34.01 min)).

Yield: 394 mg (65%), white solid. $^1$H-NMR (300 MHz, DMSO): δ=0.56–0.62 (m, 2 H), 0.87 (d, 3 H), 0.94 (d, 3 H), 1.01–1.08 (m, 2 H), 1.96–2.12 (m, 1 H), 3.95 (d, 1 H), 6.76

(d, 1 H), 7.11 (t, 1 H), 7.27 (d, 2 H), 7.56 (s, 1 H), 7.94 (d, 2 H), 8.16 (d, 2 H), 9.17 (s, 1 H)

EXAMPLE 3

N-(3-{[(4-{5-[(1S)-1-Amino-2-methylpropyl]-1,2,4-oxadiazol-3-yl}phenyl)sulphonyl]amino}phenyl)-3-fluoro-2,2-dimethylpropanamide

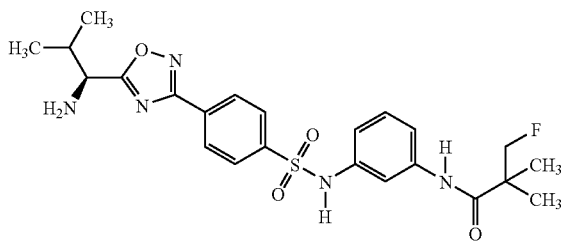

522 mg (4.04 mmol) of N,N-diisopropylethylamine, 838 mg (3.86 mmol) of Boc-Val-OH and 2.1 g (4.04 mmol) of PyBOP are introduced into 50 ml of THF, stirred at room temperature for 45 min, then treated with 1.5 g (3.67 mmol) of the amidoxime and the solution is stirred at room temperature for 16 h. The batch is then concentrated in vacuo, the residue is taken up using 200 ml of EtOAc and extracted three times with $H_2O$. The organic phase is dried over $Na_2SO_4$, filtered and the solvent is removed in vacuo. The crude product (1.8 g) is taken up in 45 ml of DMF and the solution is stirred at 110° C. for 4 h. The batch is then diluted with 100 ml of EtOAc and extracted three times with $H_2O$. The organic phase is dried over $Na_2SO_4$, filtered and the solvent is removed in vacuo. The product is purified by chromatography on silica gel 60 using cyclohexane/ethyl acetate 1:1 v/v. Yield: 1498 mg (86%), white solid.

For removal of the Boc protective groups, the product is dissolved in 10 ml of dioxane and treated with 10 ml of 4N HCl in dioxane. After 2h at 60° C., the solvent is removed in vacuo, the residue is treated with 100 ml of satd. $NaHCO_3$ solution and extracted twice with 200 ml each of EtOAc. The organic phase is dried over $Na_2SO_4$ and the solvent is removed in vacuo. The product is dried in a high vacuum and obtained analytically pure.

Yield: 910 mg (73%), white solid $^1$H-NMR (300 MHz, DMSO): δ=0.86 (d, 3 H), 0.93 (d, 3 H), 1.20 (s, 6 H), 1.96–2.11 (m, 1 H), 3.94 (d, 1 H), 4.47 (d, 2 H), 6.89 (d, 1 H), 7.13 (t, 1 H), 7.30 (d, 1 H), 7.56 (s, 1 H), 7.94 (d, 2 H), 8.26 (d, 2 H), 9.34 (s, 1 H).

| Example | Structure | MW | HPLC Rt [min] | HPLC method/ instrument | m/z fnd (M + H)+ |
|---|---|---|---|---|---|
| 4 | 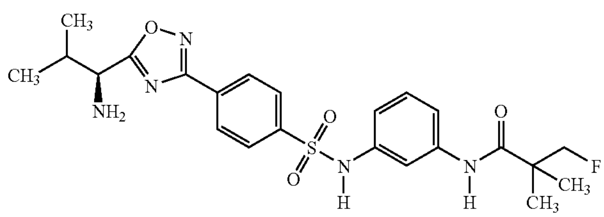 | 485.47 | 4.03 | 1 | 490 |
| 5 | 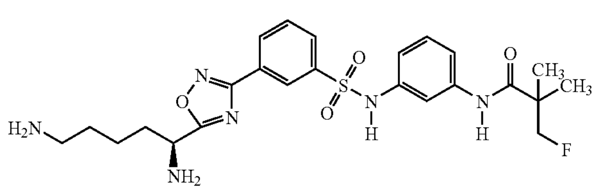 | 518.61 | 2.61 | 3 | 519 |
| 6 | 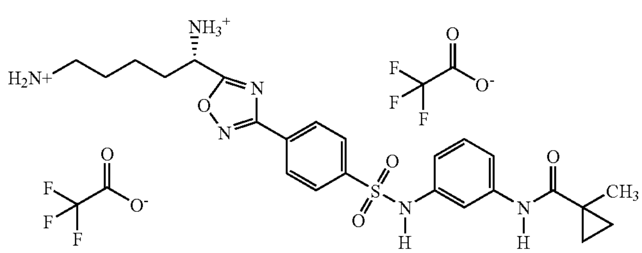 | 728.65 | 3.59 | 1 | 499 |

-continued

| Example | Structure | MW | HPLC Rt [min] | HPLC method/ instrument | m/z fnd (M + H)+ |
|---|---|---|---|---|---|
| 7 | 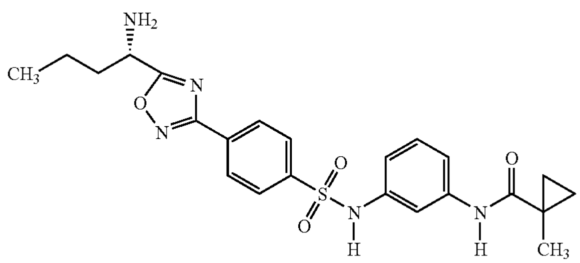 | 483.59 | 2.765 | 2 | 484 |
| 8 | 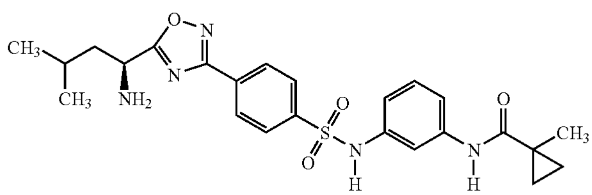 | 483.59 | 1.872 | 2 | 484 |
| 9 | 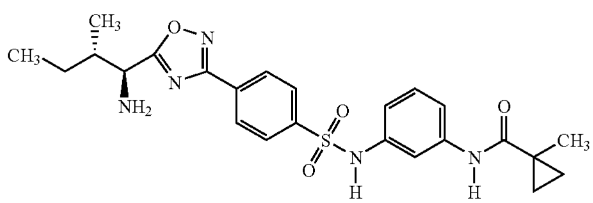 | 483.59 | 1.879 | 2 | 484 |
| 10 | 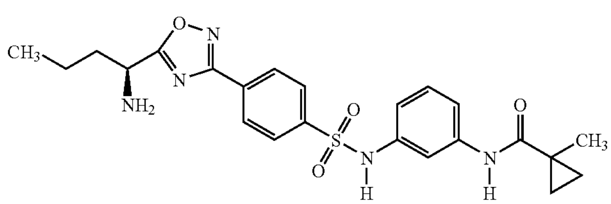 | 469.56 | 1.841 | 2 | 470 |
| 11 | 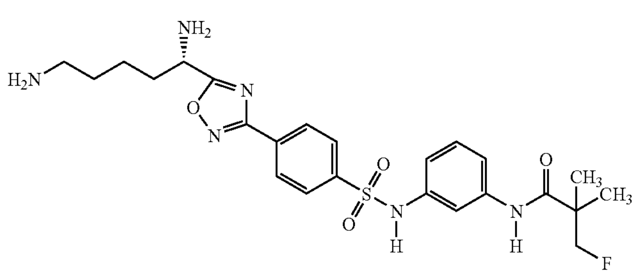 | 518.61 | 3.71 | 1 | 519 |
| 12 | 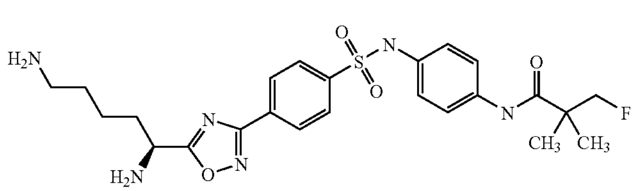 | 518.67 | 3.76 | 1 | 519 |

-continued

| Example | Structure | MW | HPLC Rt [min] | HPLC method/ instrument | m/z fnd (M + H)+ |
|---|---|---|---|---|---|
| 13 | 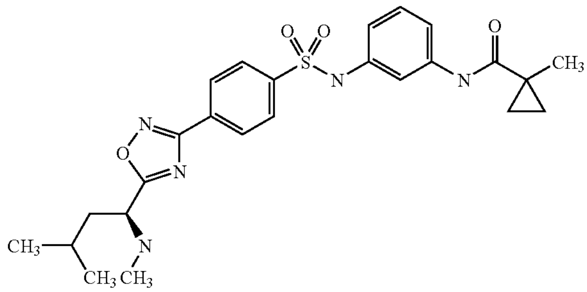 | 497.62 | 3.15 | 3 | 498.1 |
| 14 | 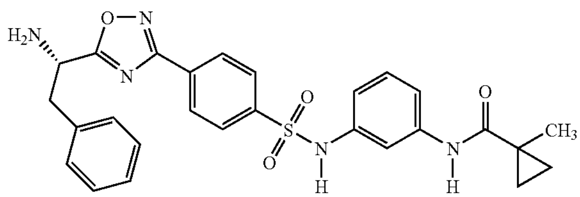 | 517.61 | 2.96 | 4 | 518 |
| 15 | 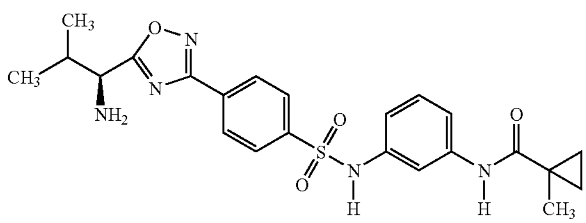 | 518.61 | 3.76 | 1 | 519 |
| 16 | 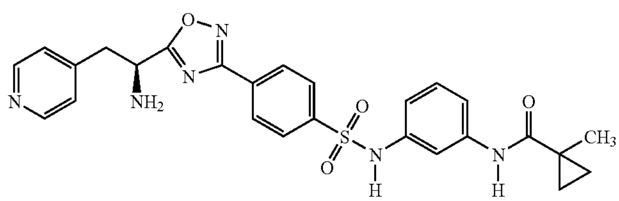 | 518.80 | 2.25 | 4 | 519 |
| 17 | 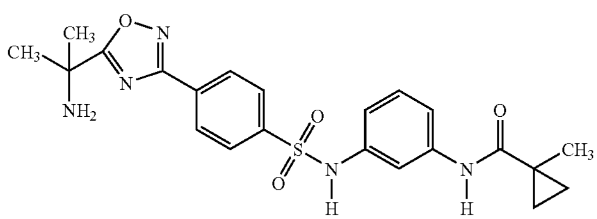 | 455.54 | 1.706 | 2 | 455 |
| 18 | 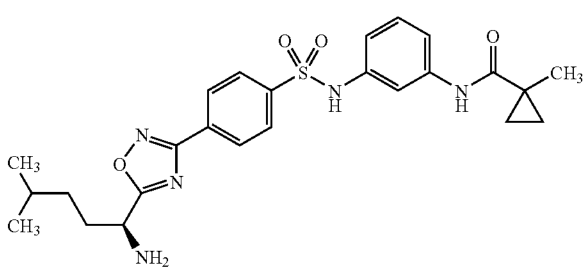 | 497.62 | 3.023 | 3 | 498 |

-continued

| Example | Structure | MW | HPLC Rt [min] | HPLC method/ instrument | m/z fnd (M + H)+ |
|---|---|---|---|---|---|
| 19 | 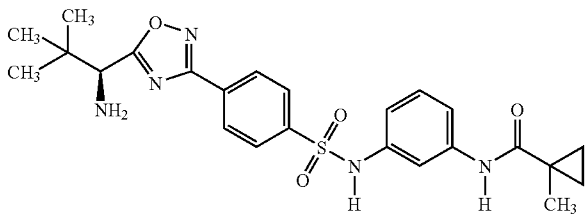 | 483.59 | 2.84 | 4 | 484 |
| 20 | 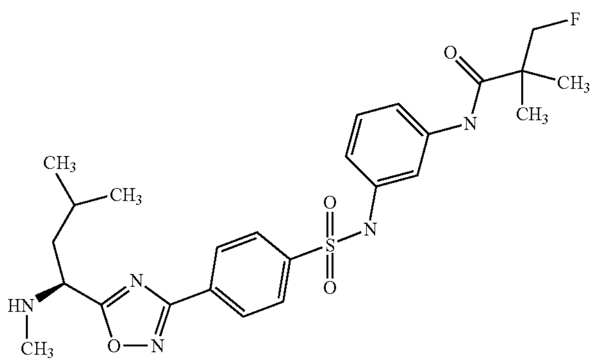 | 518.00 | 4.26 | 1 | 518 |
| 21 | 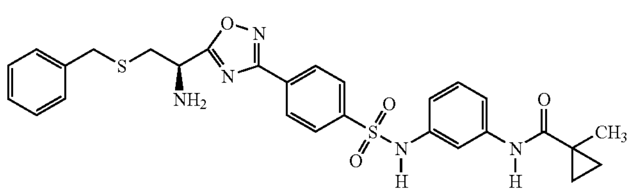 | 553.70 | 3.24 | 3 | 564 |
| 22 | 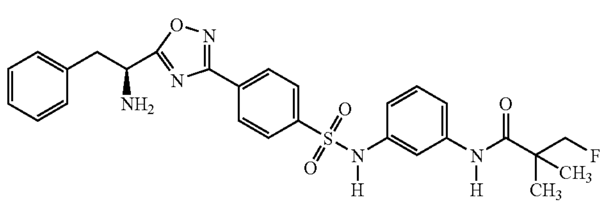 | 537.61 | 4.19 | 1 | 630 |
| 23 | 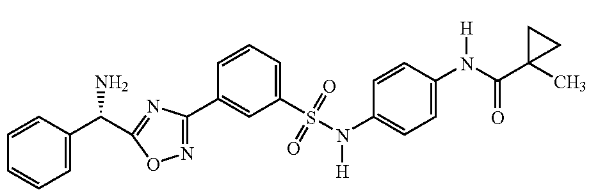 | 503.58 | 4.06 | 1 | 504 |
| 24 | 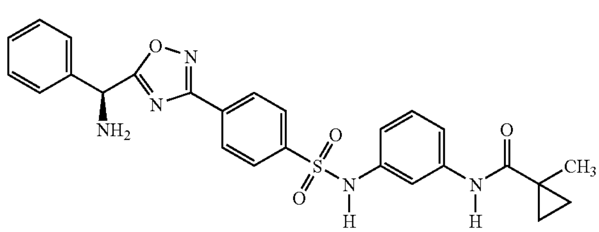 | 503.58 | 1.897 | 2 | 504 |

-continued

| Example | Structure | MW | HPLC Rt [min] | HPLC method/ instrument | m/z fnd (M + H)+ |
|---|---|---|---|---|---|
| 25 | 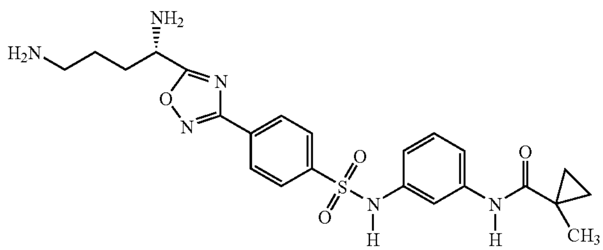 | 484.58 | 2.088 | 2 | 485 |
| 26 | 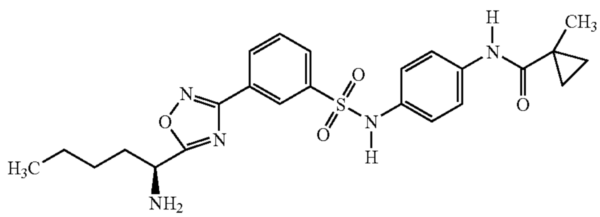 | 483.59 | 2.744 | 2 | 484 |
| 27 | 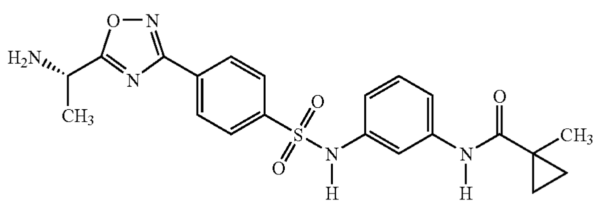 | 441.41 | 2.49 | 3 | 442 |
| 28 | 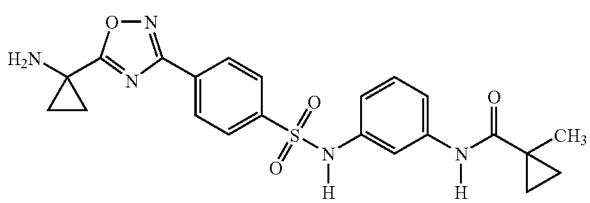 | 453.52 | 2.5 | 3 | 454 |
| 29 | 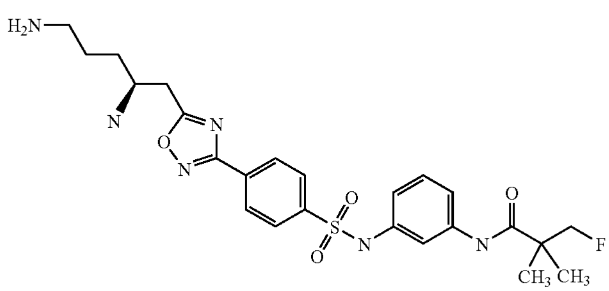 | 518.62 | 3.75 | 1 | 519 |
| 30 | 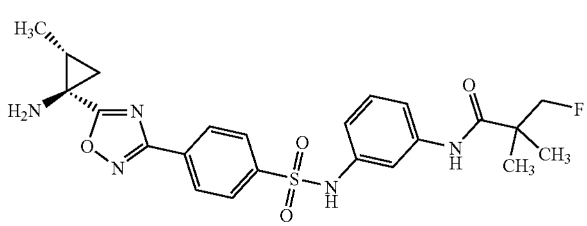 | 487.55 | 4.05 | 1 | 488 |

-continued

| Example | Structure | MW | HPLC Rt [min] | HPLC method/ instrument | m/z fnd (M + H)+ |
|---|---|---|---|---|---|
| 31 | 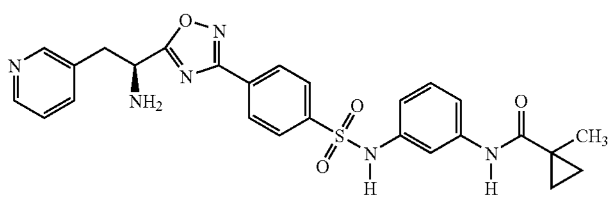 | 516.60 | 1.507 | 2 | 519 |
| 32 | 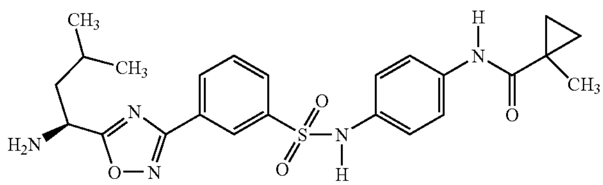 | 483.59 | 4.17 | 1 | 484 |
| 33 | 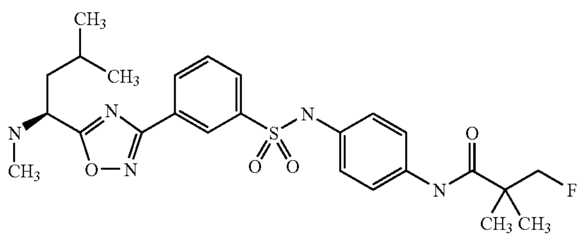 | 518.00 | 4.17 | 1 | 518 |
| 34 | 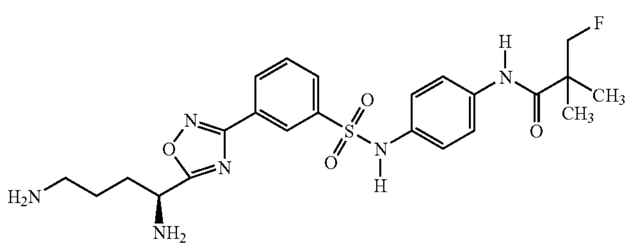 | 504.58 | 3.68 | 1 | 505 |
| 35 | 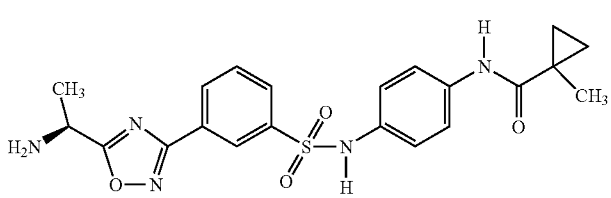 | 441.51 | 3.89 | 1 | 442 |
| 36 | 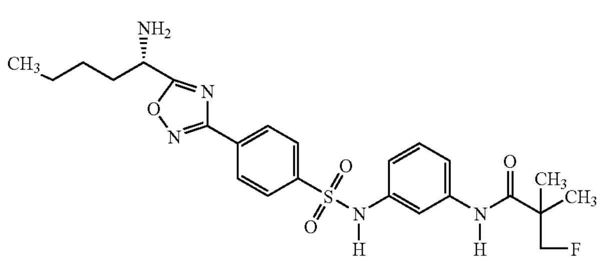 | 503.60 | 4.19 | 1 | 504 |

-continued
| Example | Structure | MW | HPLC Rt [min] | HPLC method/ instrument | m/z fnd (M + H)+ |
|---|---|---|---|---|---|
| 37 | 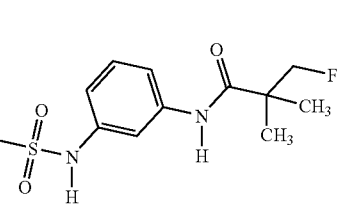 | 503.60 | 4.13 | 1 | 504 |
| 38 | 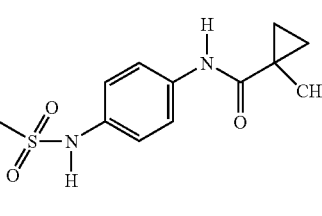 | 483.60 | 4.15 | 1 | 484 |
| 39 | 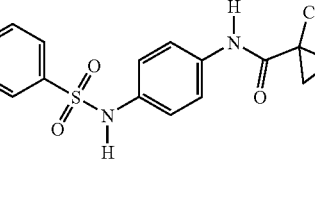 | 484.58 | 1.986 | 2 | 485 |
| 40 | 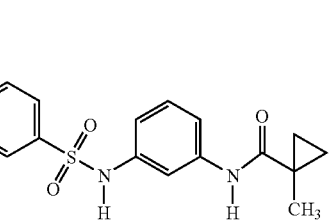 | 455.54 | 2.52 | 2 | 456 |
| 41 | 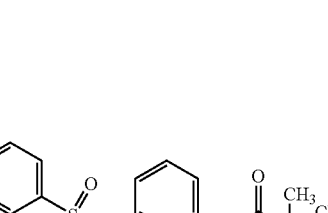 | 504.58 | 3.65 | 1 | 605 |
| 42 | 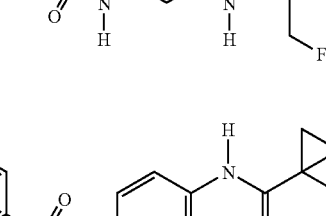 | 489.56 | 4.07 | 1 | 470 |

-continued
| Example | Structure | MW | HPLC Rt [min] | HPLC method/ instrument | m/z fnd (M + H)+ |
|---|---|---|---|---|---|
| 43 | 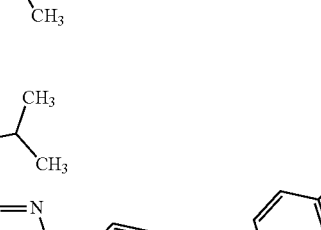 | 503.60 | 4.78 | 1 | 504 |
| 44 | 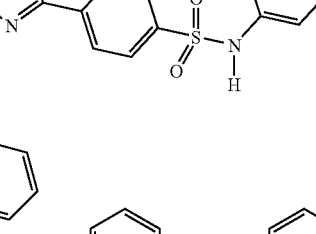 | 517.62 | 4.24 | 1 | 518 |
| 45 | 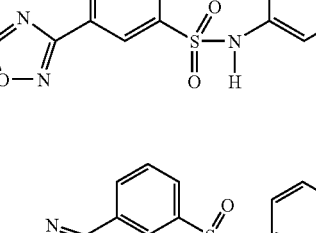 | 517.61 | 4.2 | 1 | 518 |
| 46 | 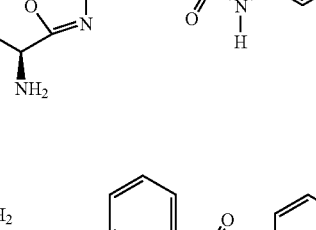 | 503.60 | 4.17 | 1 | 504 |
| 47 | 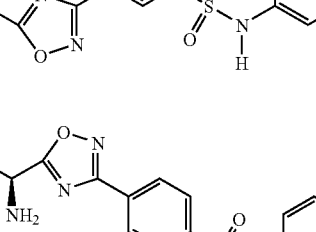 | 480.58 | 3.99 | 1 | 470 |
| 48 | 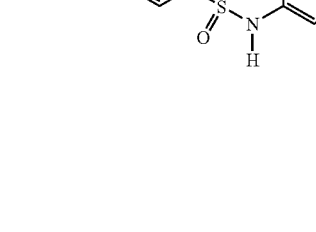 | 489.57 | 4.02 | 1 | 490 |

-continued

| Example | Structure | MW | HPLC Rt [min] | HPLC method/ instrument | m/z fnd (M + H)+ |
|---|---|---|---|---|---|
| 49 | 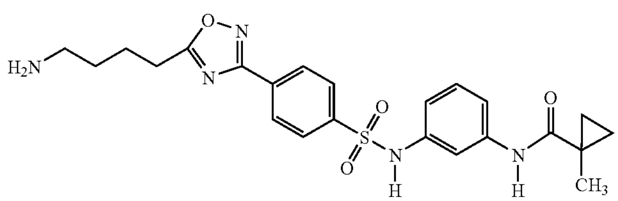 | 469.56 | 3.86 | 1 | 470 |
| 50 | 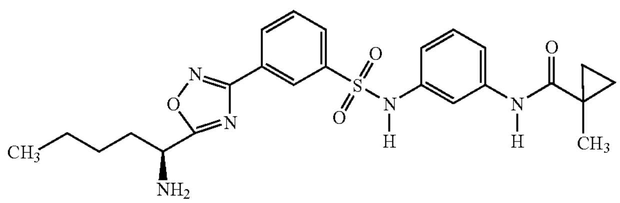 | 483.59 | 2.799 | 2 | 484 |
| 51 | 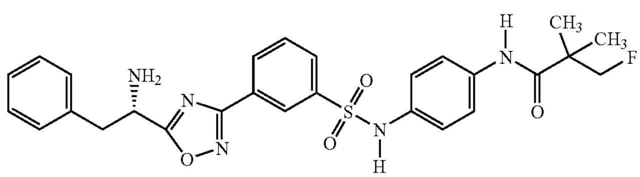 | 537.61 | 4.14 | 1 | 538 |
| 52 | 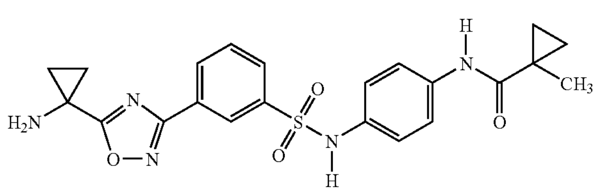 | 453.52 | 3.81 | 1 | 454 |
| 53 | 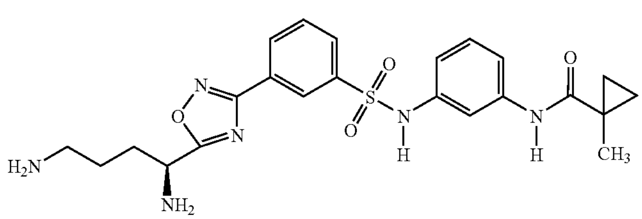 | 484.58 | 2.049 | 2 | 485 |
| 54 | 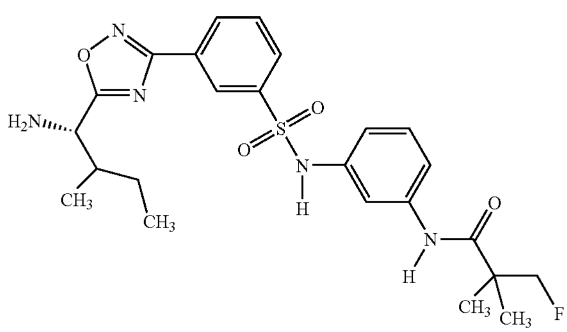 | 503.60 | 4.22 | 1 | 504 |

-continued

| Example | Structure | MW | HPLC Rt [min] | HPLC method/ instrument | m/z fnd (M + H)+ |
|---|---|---|---|---|---|
| 55 | 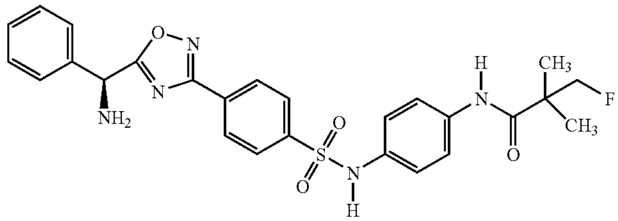 | 523.59 | 4.06 | 1 | 524 |
| 56 | 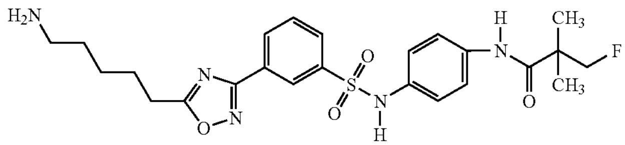 | 503.60 | 3.99 | 1 | 504 |
| 57 | 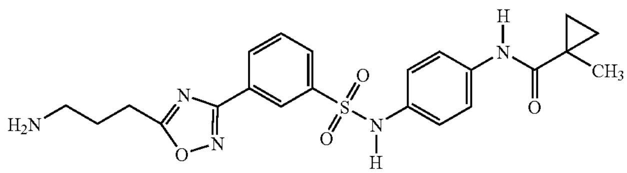 | 455.64 | 2.505 | 2 | 456 |
| 58 | 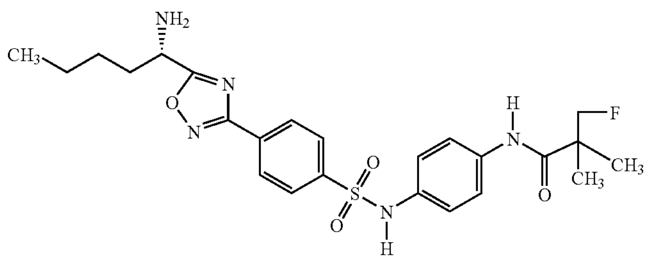 | 503.60 | 2.765 | 2 | 604 |
| 59 | 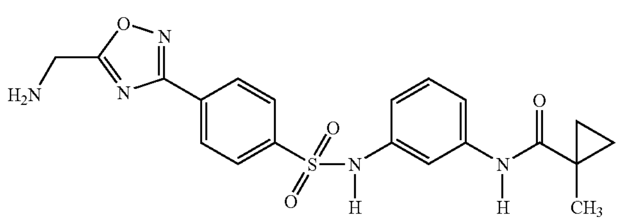 | 427.48 | 2.417 | 2 | 428 |
| 60 | 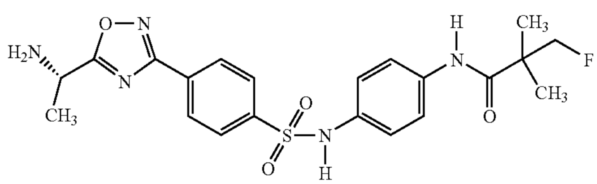 | 451.52 | 3.82 | 1 | 482 |
| 61 | 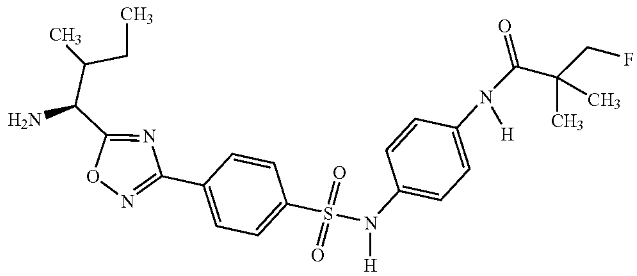 | 503.60 | 4.18 | 1 | 504 |

| Example | Structure | MW | HPLC Rt [min] | HPLC method/ instrument | m/z fnd (M + H)+ |
|---|---|---|---|---|---|
| 62 | 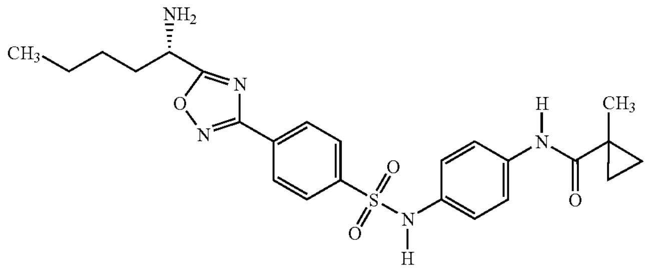 | 483.59 | 2.749 | 2 | 484 |
| 63 | 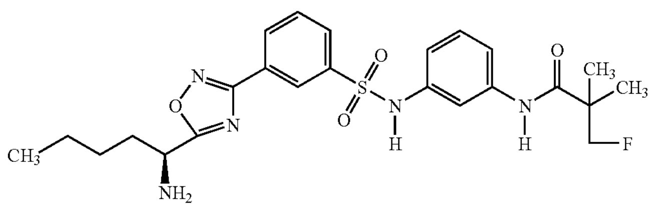 | 503.60 | 2.828 | 2 | 604 |
| 64 | 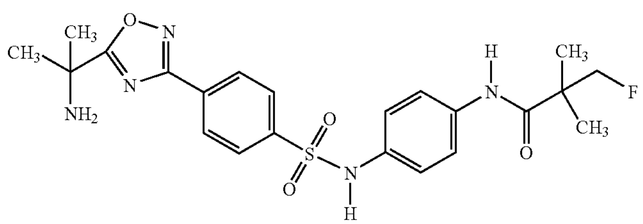 | 475.64 | 3.88 | 1 | 476 |
| 65 | 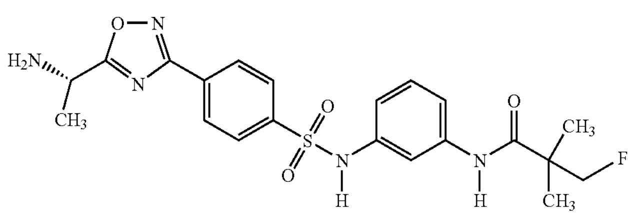 | 461.52 | 3.84 | 1 | 462 |
| 66 | 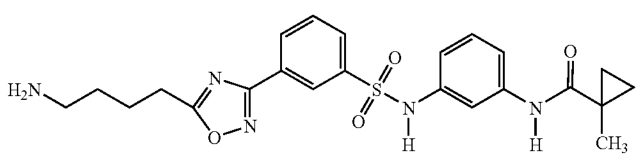 | 469.56 | 2.64 | 2 | 470 |
| 67 | 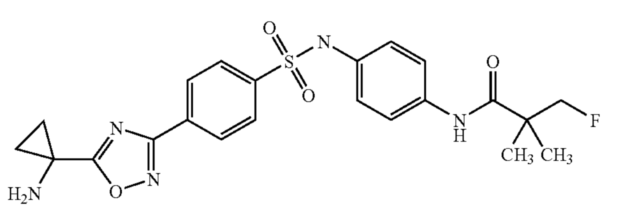 | 473.53 | 3.69 | 1 | 474 |
| 68 | 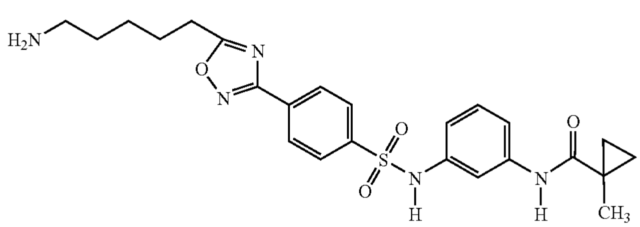 | 483.59 | 2.85 | 4 | 484.6 |

-continued

| Example | Structure | MW | HPLC Rt [min] | HPLC method/ instrument | m/z fnd (M + H)+ |
|---|---|---|---|---|---|
| 69 | 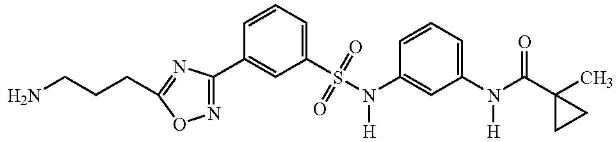 | 455.54 | 2.548 | 2 | 456 |
| 70 | 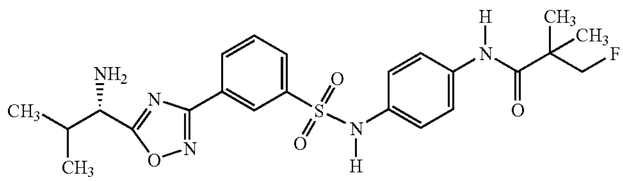 | 489.47 | 3.98 | 1 | 490 |
| 71 | 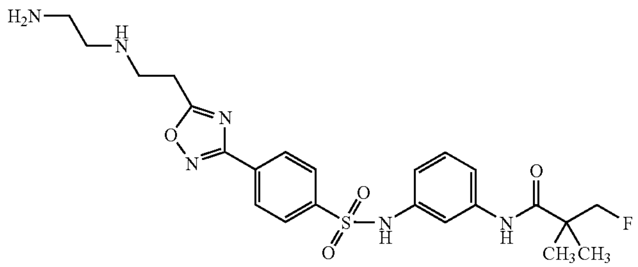 | 504.58 | 3.85 | 1 | 505 |
| 72 | 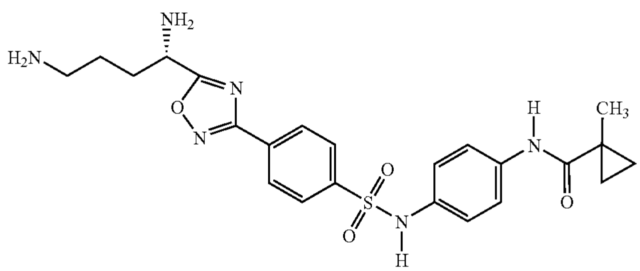 | 484.58 | 1.981 | 2 | 485 |
| 73 | 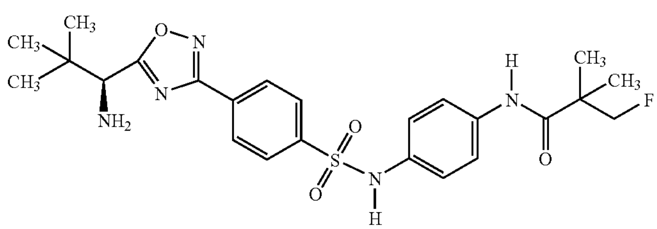 | 503.60 | 4.04 | 1 | 504 |
| 74 | 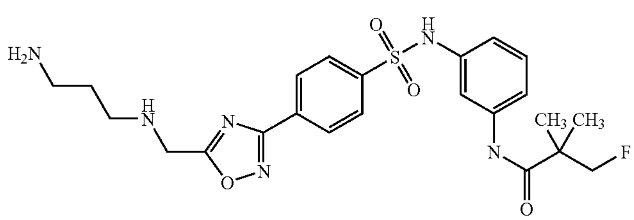 | 504.58 | 3.79 | 1 | 505 |
| 75 | 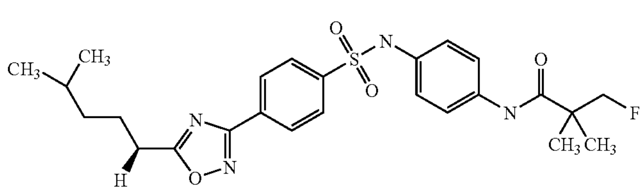 | 517.52 | 4.19 | 1 | 518 |

-continued

| Example | Structure | MW | HPLC Rt [min] | HPLC method/ instrument | m/z fnd (M + H)⁺ |
|---------|-----------|------|------|---|-----|
| 76 | 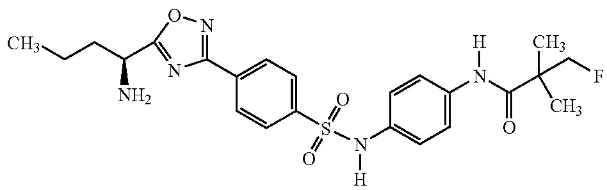 | 489.57 | 4.06 | 1 | 490 |
| 77 | 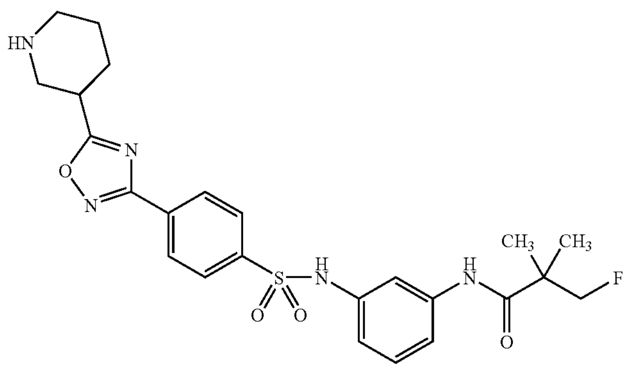 | 501.58 | 3.93 | 1 | 502 |
| 78 | 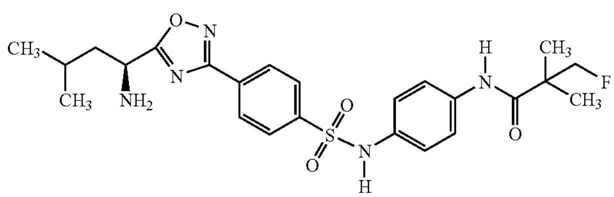 | 503.60 | 4.1 | 1 | 504 |
| 79 | 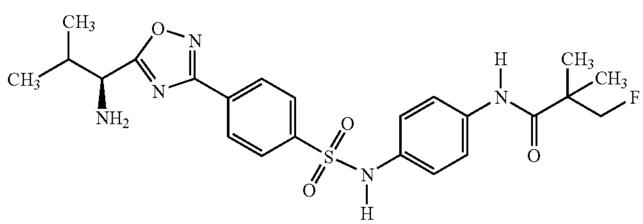 | 489.57 | 3.98 | 1 | 490 |
| 80 | 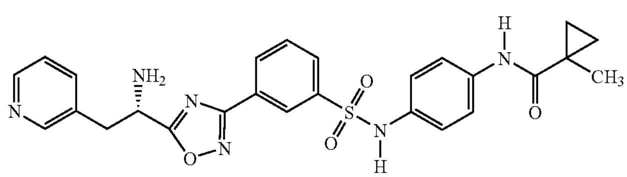 | 515.60 | 3.78 | 1 | 519 |
| 81 | 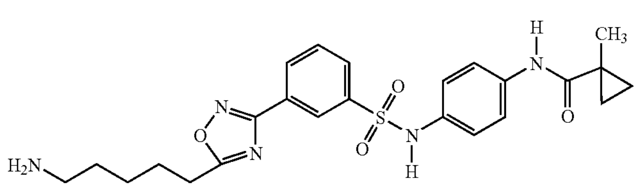 | 483.59 | 2.82 | 4 | 484 |
| 82 | 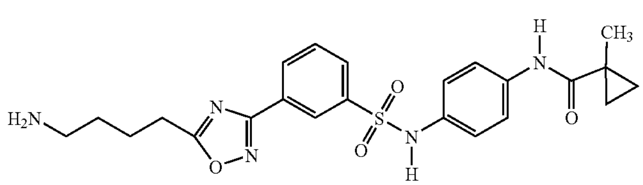 | 469.56 | 2.522 | 2 | 470 |

-continued

| Example | Structure | MW | HPLC Rt [min] | HPLC method/ instrument | m/z fnd (M + H)+ |
|---|---|---|---|---|---|
| 83 | 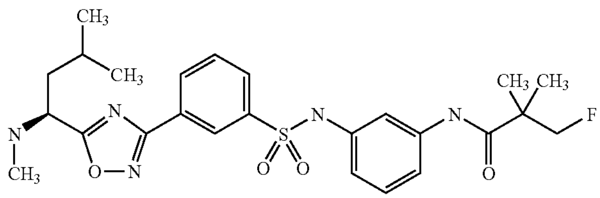 | 518.00 | 4.2 | 1 | 518 |
| 84 | 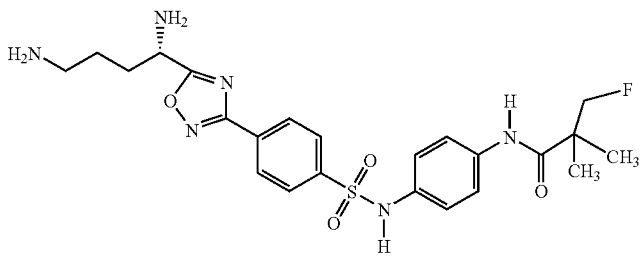 | 504.58 | 2.053 | 2 | 505 |
| 85 | 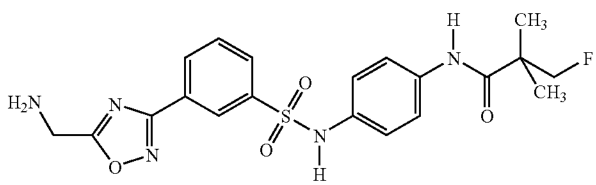 | 447.49 | 3.78 | 1 | 448 |
| 86 | 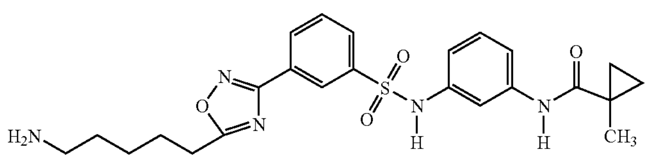 | 483.59 | 2.84 | 4 | 484 |
| 87 | 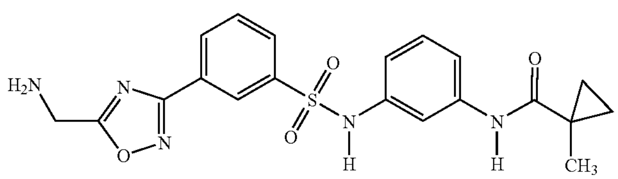 | 427.48 | 2.428 | 2 | 428 |
| 88 | 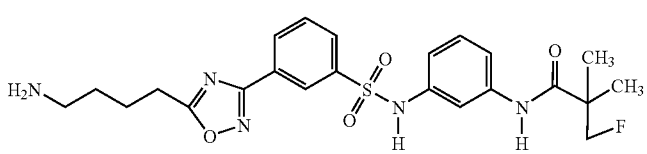 | 489.57 | 2.58 | 2 | 490 |
| 89 | 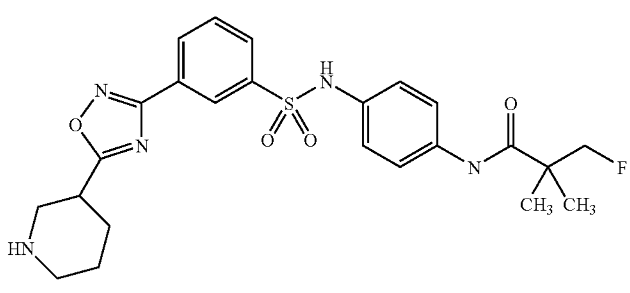 | 501.58 | 3.91 | 1 | 502 |

-continued

| Example | Structure | MW | HPLC Rt [min] | HPLC method/ instrument | m/z fnd (M + H)+ |
|---|---|---|---|---|---|
| 90 | 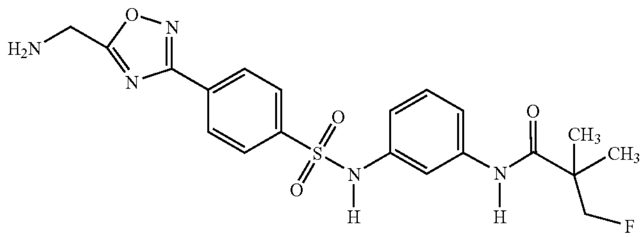 | 447.49 | 3.78 | 1 | 448 |
| 91 | 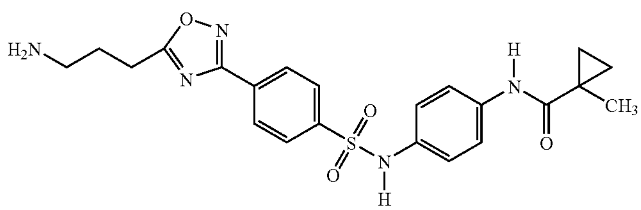 | 455.54 | 2.547 | 2 | 456 |
| 92 | 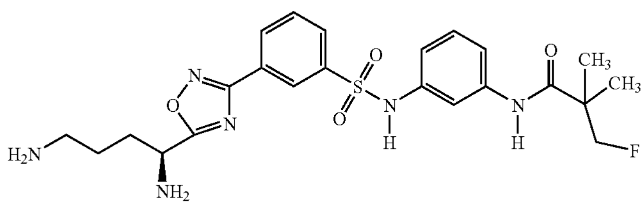 | 504.58 | 2.017 | 2 | 505 |
| 93 | 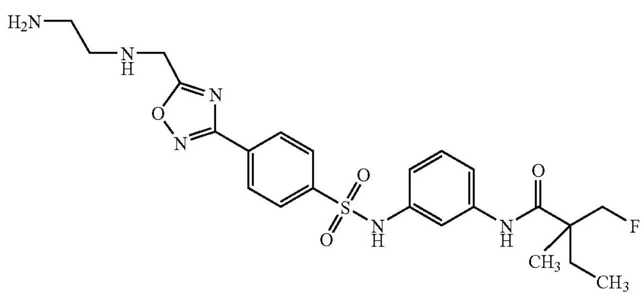 | 490.56 | 3.72 | 1 | 491 |
| 94 | 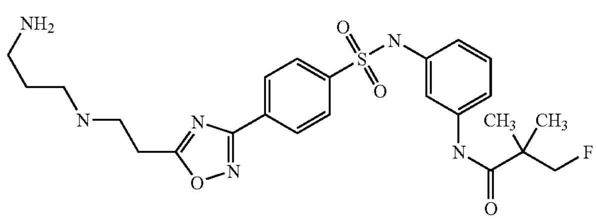 | 518.81 | 3.83 | 1 | 519 |
| 95 | 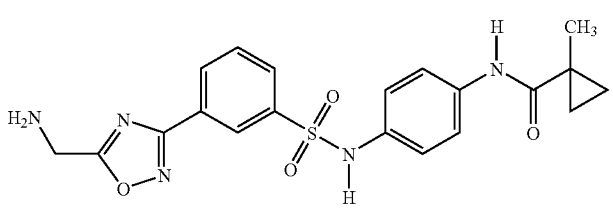 | 427.48 | 2.407 | 2 | 428 |
| 96 | 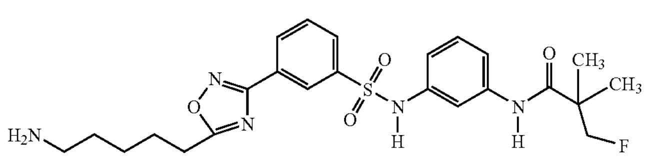 | 503.60 | 2.8 | 4 | 504 |

| Example | Structure | MW | HPLC Rt [min] | HPLC method/ instrument | m/z fnd (M + H)+ |
|---|---|---|---|---|---|
| 97 | 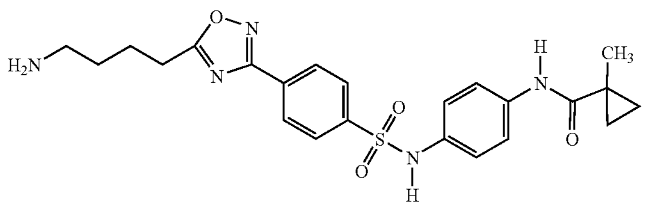 | 459.58 | 2.512 | 2 | 470 |
| 98 | 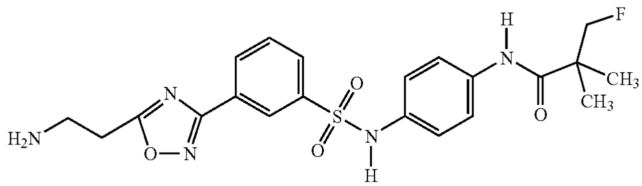 | 451.52 | 2.58 | 4 | 462 |
| 99 | 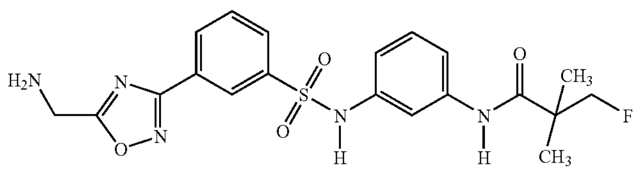 | 447.49 | 2.431 | 2 | 448 |
| 100 | 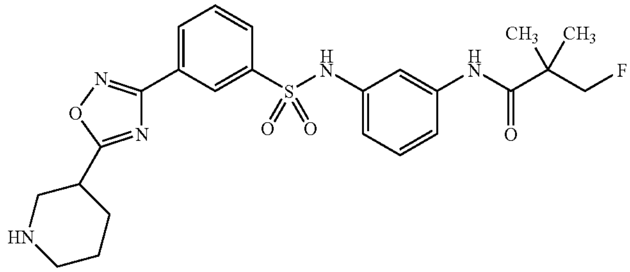 | 501.58 | 3.94 | 1 | 502 |
| 101 | 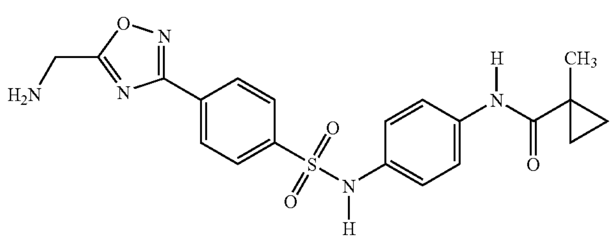 | 427.48 | 2.393 | 2 | 428 |
| 102 | 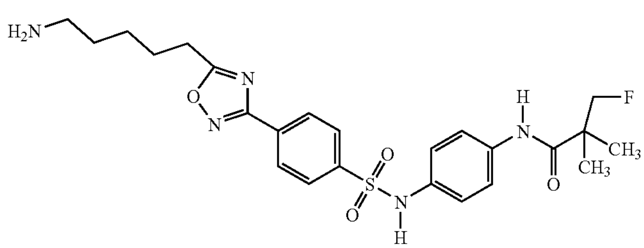 | 503.60 | 2.77 | 4 | 504.5 |
| 103 | 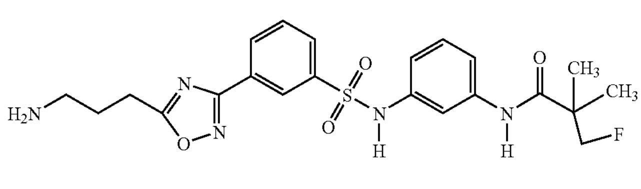 | 475.54 | 2.57 | 2 | 476 |

-continued

| Example | Structure | MW | HPLC Rt [min] | HPLC method/ instrument | m/z fnd (M + H)+ |
|---|---|---|---|---|---|
| 104 | 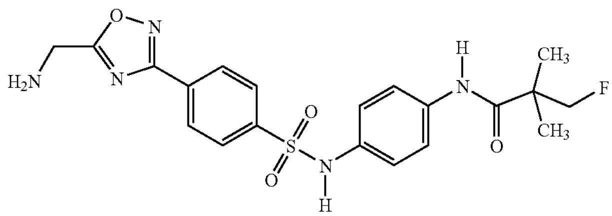 | 447.49 | 2.409 | 2 | 448 |
| 105 | 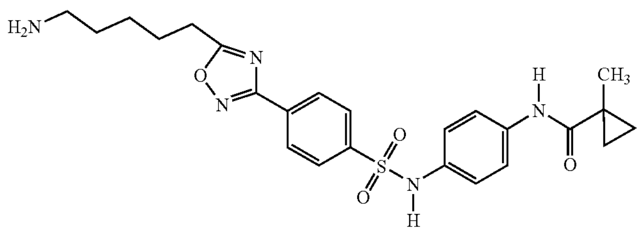 | 483.59 | 2.82 | 4 | 484 |
| 106 | 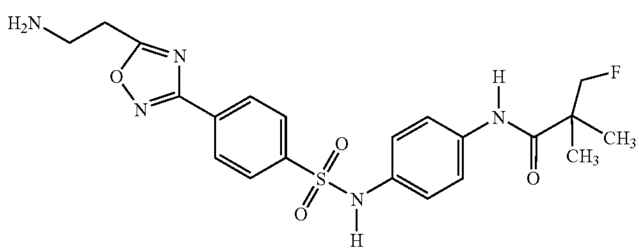 | 481.52 | 2.488 | 2 | 462 |

TABLE 2

The compounds mentioned in the working examples and tables were characterized using the LC-MS and HPLC processes described below:

Method 1:

Column: Kromasil C18 60*2, L-R temperature: 30° C., flow = 0.75 ml min$^{-1}$, eluent: A = 0.005 M HClO$_4$, B = CH$_3$CN, gradient: → 0.5 min 98% A → 4.5 min 10% A → 6.5 min 10% A Method 2:

Column: Symmetry C18 2.1 × 150 mm, column oven: 50° C., flow = 0.9 ml min$^{-1}$, eluent: A = 0.3 g 30% strength HCl/1 water, B = CH$_3$CN, gradient: 0.0 min 90% A → 3.0 min 10% A → 6.0 min 10% A Method 3:

HP1100, column: LiChroCart 75-5 LiChrospher 100 RP-18 5 µm, column oven: 40° C., flow = 2.5 ml min$^{-1}$, eluent: A = water containing 0.05% of TFA, B = CH$_3$CN containing 0.05% of TFA, gradient: 0.0 min 90% A → 0.05 min 90% A → 5.0 min 5% A → 7.0 min 5% A → 7.05 min 90% A → 8.0 min 90% A Method 4:

LC-MS: MHZ-2P, instrument Micromass Platform LCZ
Column: Symmetry C18 50 mm × 2.1 mm, 3.5 µm, temperature: 40° C., flow = 0.5 ml min$^{-1}$, eluent A = CH$_3$CN + 0.1% of formic acid, eluent B = water + 0.1% of formic acid, gradient: 0.0 min 10% A → 4 min 90% A → 6 min 90% A

The invention claimed is:

1. A compound of the general formula (I)

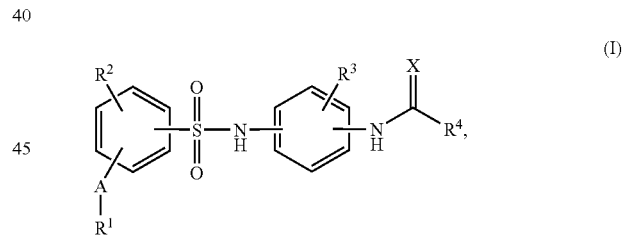

in which

R$^2$ and R$^3$ are identical or different and represent hydrogen, hydroxyl, halogen, nitro, cyano, trifluoromethyl, trifluoromethoxy, (C$_1$–C$_6$)-alkyl, (C$_1$–C$_6$)-alkoxy or a group of the formula

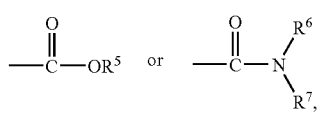

in which

R$^5$, R$^6$ and R$^7$ are identical or different and in each case represent hydrogen or (C$_1$–C$_6$)-alkyl, which for its part can be substituted by one or two substituents selected from the group consisting of hydroxyl, halogen, cyano, trifluoromethyl and trifluoromethoxy, A represents a five- or six-membered heteroaryl linked via a C atom to the adjacent phenyl ring, $R^1$ represents the radical

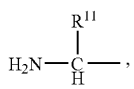

in which
$R^{11}$ represents the side group of an amino acid, and the amino group in $R^1$ can optionally be mono- or polysubstituted by $(C_1-C_6)$alkyl, alkylcarbonyl, or phenyl, or $R^1$ represents a straight-chain or branched $(C_1-C_5)$-alkyl radical, which for its part can be substituted by one or more groups selected from phenyl, piperidinyl, pyridinyl, thiazolyl, thienyl,

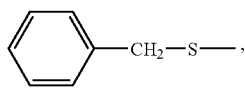

or a group

in which
$R^{12}$ and $R^{13}$ are identical or different and can represent hydrogen, $(C_1-C_6)$alkyl, alkylcarbonyl, an amino protective group, or phenyl, or $R^1$ represents a radical

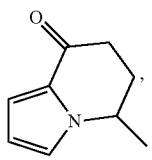

or $R^1$ represents a straight-chain or branched $(C_1-C_5)$-alkyl radical, which for its part is substituted by a group

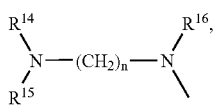

in which
$R^{14}$, $R^{15}$, $R^{16}$ are identical or different and represent hydrogen or $(C_1-C_6)$alkyl and
n can assume the values 2 or 3, or $R^1$ represents piperidinyl or the radical

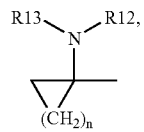

in which
$R^{12}$ and $R^{13}$ have the meaning indicated above,
n represents a number from 1 to 4 and the ring can be up to trisubstituted in an identical or different manner by halogen, $(C_1-C_6)$-alkyl, halogeno-$(C_1-C_6)$-alkyl, amino, or hydroxyl, $R^4$ represents tert-butyl, which is optionally up to trisubstituted, in an identical or different manner, by hydroxyl, fluorine or chlorine, or represents cyclopropyl or cyclobutyl, which are mono- to trisubstituted in an identical or independent manner by halogen or $(C_1-C_6)$-alkyl, $(C_1-C_6)$-alkyl optionally being substituted by hydroxyl, fluorine or chlorine, and in which
X represents oxygen or sulphur,
and in which nitrogen-containing heterocycles can also be present as N-oxides, or a tautomer, stereoisomer, or mixture of stereoisomers of said compound, or a pharmacologically tolerable salt of said compound, tautomer, stereoisomer, or mixture of stereoisomers.

2. The compound of the general formula (I) according to claim 1,
in which
$R^2$ and $R^3$ are identical or different and represent hydrogen or halogen,
A represents the radical (A-I)

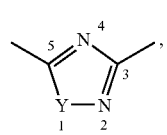

(A-I)

which is linked via one of the carbon atoms of positions 3 or 5 to the adjacent phenyl ring,
and in which
Y represents oxygen,
or
A represents the radical (A-II)

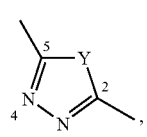

(A-II)

which is linked via one of the carbon atoms of positions 2 or 5 to the adjacent phenyl ring, and in which
Y represents oxygen,
$R^1$ represents the radical

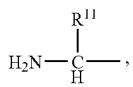

in which
$R^{11}$ represents the side group of an amino acid, and the amino group in $R^1$ can optionally be mono- or polysubstituted by $(C_1-C_6)$-alkyl, alkylcarbonyl, an amino protective group, or phenyl,
or
$R^1$ represents a straight-chain or branched $(C_1-C_5)$-alkyl radical, which for its part can be substituted by one or more groups selected from phenyl, piperidinyl, pyridinyl, thiazolyl, thienyl,

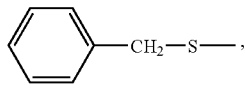

a group

in which
$R^{12}$ and $R^{13}$ are identical or different and can represent hydrogen, $(C_1-C_6)$-alkyl, alkylcarbonyl, an amino protective group, or phenyl,
or
$R^1$ represents a straight-chain or branched $(C_1-C_5)$-alkyl radical, which for its part is substituted by a group

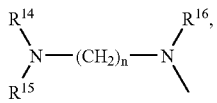

in which
$R^{14}$, $R^{15}$, $R^{16}$ are identical or different and represent hydrogen or methyl
and
n can assume the values 2 or 3,
or
$R^1$ represents piperidin-3-yl or the radical

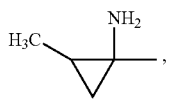

$R^4$ represents tert-butyl, which is optionally up to trisubstituted, in an identical or different manner, by hydroxyl, fluorine or chlorine, or represents cyclopropyl or cyclobutyl, which is substituted in the α-position to the carbonyl group or thiocarbonyl group by methyl, which for its part is optionally substituted by hydroxyl, fluorine or chlorine,
and in which
X represents oxygen,
and in which nitrogen-containing heterocycles can also be present as N-oxides,
or a tautomer, stereoisomer or mixture of stereoisomers of said compound, or a pharmacologically tolerable salt of said compound tautomer, stereoisomer, or mixture of stereoisomers.

3. The compound of the general formula (I) according to claim 1,
in which
$R^2$ and $R^3$ represent hydrogen,
A represents one of the radicals

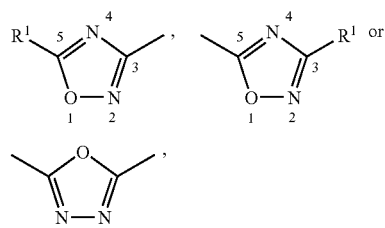

$R^1$ represents the radical

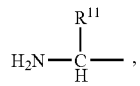

in which
$R^{11}$ represents the side group of an amino acid, and the amino group in $R^1$ can optionally be mono- or polysubstituted by methyl, alkylcarbonyl, an amino protective group, or phenyl,
or
$R^1$ represents a straight-chain or branched $(C_1-C_5)$-alkyl radical, which for its part can be substituted by one or more groups selected from phenyl, piperidinyl, pyridinyl, thiazolyl, thienyl,

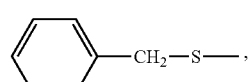

or a group

in which
$R^{12}$ and $R^{13}$ are identical or different and can represent hydrogen, methyl, alkylcarbonyl, an amino protective group, or phenyl, or R$^1$ represents a straight-chain or branched (C$_1$–C$_5$) alkyl radical, which for its part is substituted by a group $$R^{14}\!\!-\!\!\underset{R^{15}}{N}\!\!-\!\!(CH_2)_n\!\!-\!\!\underset{}{N}\!\!-\!\!R^{16},$$

in which
R$^{14}$, R$^{15}$, R$^{16}$ are identical or different and represent hydrogen or methyl
and
n can assume the values 2 or 3, or R$^1$ represents piperidin-3-yl or the radical

[structure with H$_3$C, NH$_2$ on cyclopropane]

R$^4$ represents tert-butyl, which is optionally up to trisubstituted, in an identical or different manner, by hydroxyl, fluorine or chlorine, or
represents cyclopropyl or cyclobutyl, which is substituted in the α-position to the carbonyl group or thiocarbonyl group by methyl, which for its part is optionally substituted by hydroxyl, fluorine or chlorine,
and in which
X represents oxygen,
and in which nitrogen-containing heterocycles can also be present as N-oxides,
or a tautomer, stereoisomer, or mixture of stereoisomers of said compound or a pharmacologically tolerable salt of said compound, tautomer, stereoisomer, or mixture of stereoisomers.

4. The compound of the general formula (I) according to claim 1,
in which
R$^4$ represents one of the radicals

[two structures: methylcyclopropyl or neopentyl-F]

5. A compound of the general formula (Ia)

(Ia)

[structure with R$^1$, A, R$^2$, R$^3$, X, R$^4$, sulfonamide-amide]

in which
R$^1$, R$^2$, R$^3$, R$^4$, A and X have the meanings indicated above in claim 1.

6. The compound of the general formula (I) according to claim 1,
in which
A represents a 3-linked 1,2,4-oxadiazole.

7. The compound of the general formula (I) according to claim 1, which is selected from the group consisting of the following compounds:

[structure 1: with H$_2$N, oxadiazole, sulfonamide, cyclopropyl-CH$_3$ amide]

[structure 2: with H$_2$N, H$_3$C-CH-CH$_3$, oxadiazole, sulfonamide, cyclopropyl-CH$_3$ amide]

and

[structure 3: with H$_3$C-CH-CH$_3$, H$_2$N, oxadiazole, sulfonamide, F, CH$_3$, CH$_3$ amide]

8. A process for the preparation of compounds of the general formula (I) according to claim 1, in which a compound of the general formula (D-1)

(D-1)

[structure with HO-N, H$_2$N, R$^2$, sulfonamide, R$^3$, X, R$^4$]

in which
X, R$^2$, R$^3$ and R$^4$ have one of the meanings indicated above in claim 1,
is acylated with a carboxylic acid of the general formula (E-1)

R$^1$—COOH     (E-1)

in which
R$^1$ has the meaning indicated above in claim 1 and free amino groups contained in R$^1$ are present protected by amino protective groups,
in the presence of a condensing agent and of a base, and the acylated amidoxime is cyclized to the 1,2,4-oxadiazole.

9. A process for the preparation of compounds of the general formula (I) according to claim 1, in which a compound of the general formula (G-2)

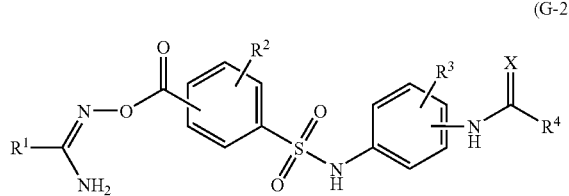

in which
R¹, R², R³, R⁴ and X have the meaning indicated above in claim 1,
are cyclized.

10. A compound of the general formula (D-1)

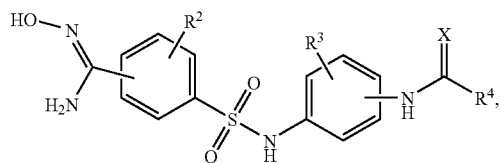

in which R², R³, R⁴ and X have the meanings indicated in claim 1.

11. A compound of the general formula (G-2)

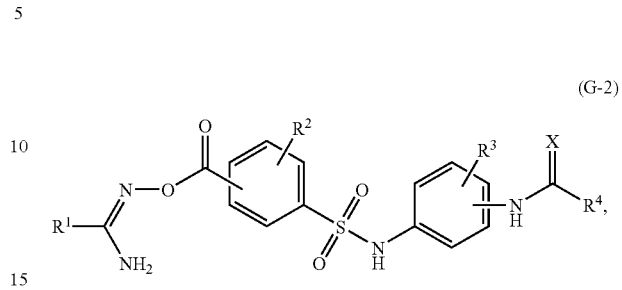

in which $R^1$, $R^2$, $R^3$, $R^4$ and X have the meanings indicated in claim 1.

12. A pharmaceutical composition comprising a compound of the general formula (I) according to any one of claims 1 to 7.

13. A method for the treatment of cytomegalovirus infection, comprising administering an effective amount of a compound of claim 1.

* * * * *